(12) United States Patent
Besse et al.

(10) Patent No.: US 7,569,274 B2
(45) Date of Patent: Aug. 4, 2009

(54) IMPREGNATED POWDER IMPROVING BIOAVAILABILITY AND/OR SOLUBILITY AND METHOD OF PRODUCTION

(75) Inventors: Jérôme Besse, Listrac Medoc (FR); Laurence Besse, Listrac Medoc (FR); Myriam Alphonse, Bordeaux (FR)

(73) Assignee: SAS Galenix Innovations, Saint-Jean D'Illac (FR)

( * ) Notice: Subject to any disclaimer, the term of this patent is extended or adjusted under 35 U.S.C. 154(b) by 638 days.

(21) Appl. No.: 10/547,797

(22) PCT Filed: Mar. 5, 2004

(86) PCT No.: PCT/FR2004/000541

§ 371 (c)(1), (2), (4) Date: Sep. 6, 2005

(87) PCT Pub. No.: WO2004/080381

PCT Pub. Date: Sep. 23, 2004

(65) Prior Publication Data

US 2006/0182691 A1    Aug. 17, 2006

(30) Foreign Application Priority Data

Mar. 6, 2003   (FR) .................................. 03 02802

(51) Int. Cl.
B32B 5/66    (2006.01)

(52) U.S. Cl. ....................... 428/403; 428/404; 428/405; 428/406; 428/407; 427/212; 427/213.3

(58) Field of Classification Search ................. 428/403, 428/404, 405, 406, 407; 427/212, 213.3
See application file for complete search history.

(56) References Cited

FOREIGN PATENT DOCUMENTS

WO    WO03/051334    *   6/2003

* cited by examiner

*Primary Examiner*—Leszek Kiliman
(74) *Attorney, Agent, or Firm*—Arent Fox LLP

(57) ABSTRACT

This invention relates to an impregnated powder for increasing the bioavailabilty and/or the solubility of at least one active principle comprising a solid, inert support in a particle form impregnated by a liquid medium comprising a hydrophobic phase and optionally a hydrophilic phase, at least one surfactant and at least one active principle dissolved in at least one of said phases, wherein said active principle(s) is(are) also present in at least one of said phases in the form of a suspension.

Figure 1:
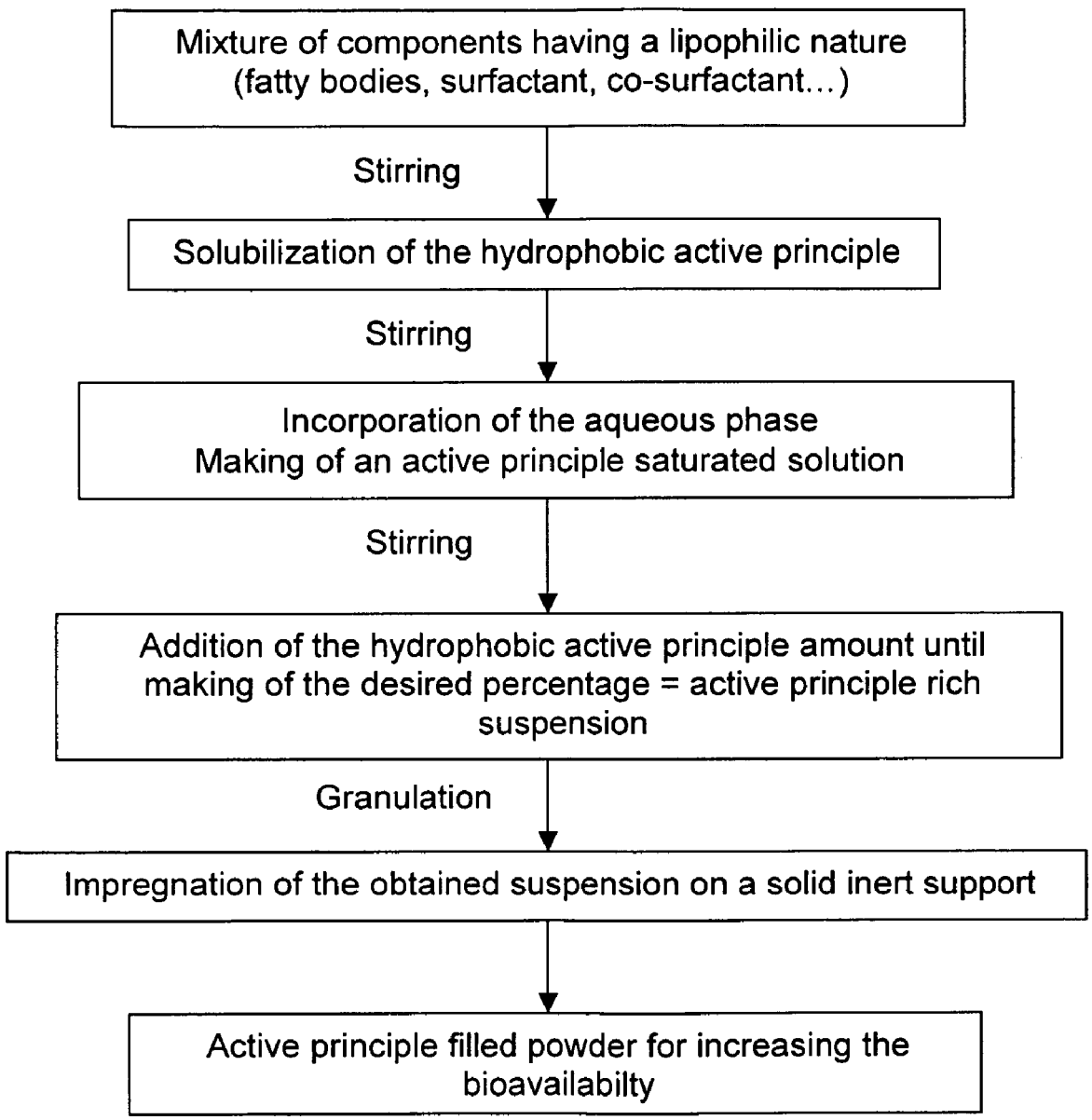

Such an impregnated powder is used as a base for various preparations in the pharmaceutical, parapharmaceutical and cosmetic field, in the food complement field and in the food processing industry.

31 Claims, 12 Drawing Sheets

IMPREGNATED POWDER IMPROVING BIOAVAILABILITY AND/OR SOLUBILITY AND METHOD OF PRODUCTION

CROSS-REFERENCE TO RELATED APPLICATION

This application is a National Stage entry of International Application Number PCT/FR2004/000541, filed Mar. 5, 2004. The disclosure of the prior application is hereby incorporated herein in its entirety by reference.

FIELD OF THE INVENTION

This invention relates to a method for producing an impregnated powder for increasing the bioavailability and/or the solubilization of one or more active principle(s) or making easier the administration mode thereof, cheap to manufacture and easy to implement. The active principle(s) may belong to the pharmaceutical, parapharmaceutical and cosmetic field, to the field of personal care, food complements or food processing industry, being liposoluble and/or hydrosoluble. Such a powder is impregnated with a liquid based on one or more active principle(s). Such a liquid may optionally have the form of a solution and a dispersed system.

BACKGROUND OF THE INVENTION

The bioavailability corresponds to the active principle amount being administered reaching the systemic circulation. The efficiency of an active principle depends on the bioavailability thereof.

Many active principles suffer, through the oral route, from a low bioavailability.

Before reaching the vena cava, an active principle is conveyed through the gastrointestinal tract and passes through the intestine wall and the liver. At the liver level, the active principles may be metabolised in an inactive form and are subjected to the effect of the first hepatic passage before reaching the systemic circulation. Such an effect of the first hepatic passage is responsible for the low oral bioavailability of most of the active principles.

Another cause of the low bioavailability is the low solubility of the active principles, which are particularly little hydrosoluble. The absorption mode is then very long or incomplete leading to random therapeutic responses.

The low residence time in the gastrointestinal tract can also lead to a low bioavailability. If the active principle is not quickly dissolved or cannot penetrate into the epithelial membrane (this is the case of a highly ionized or polar active), the absorption time may be insufficient. In such a case, the bioavailability is variable and very low. Another cause for the low bioavailability is attributed to the competitive reactions of the absorption phenomenon, i.e. the complex formation, the hydrolysis by the gastric acid or the digestive enzymes, the conjugation in the intestine wall, the absorption of other active principles, the metabolism through luminal microflora.

For further information regarding the bioavailability, refer to Merck Manual of diagnostic and therapy, section 22, Clinical pharmacology; chapter 298.

The physicochemical properties of the active principles govern the absorption potential thereof, however the properties of the galenic form being implemented widely determine the bioavailability and/or the solubility of the active principle.

An object of the invention is therefore an impregnated powder for increasing the bioavailability and/or the solubility such as previously defined, and more particularly allowing to increase the absorption, the solubility and/or the protection of the active principle in order to facilitate the administration of liposoluble and/or hydrosoluble molecules (generally with a low bioavailability), easy and cheap to manufacture, in contrast to the lyophilization and spraying method generally used in the prior art for adsorbing fat bodies on a solid support.

An object of the invention is a powder for increasing the bioavailability and/or the solubility of at least one active principle comprising a solid inert support, in a particle form impregnated by a liquid medium comprising a hydrophobic phase and a hydrophilic phase, at least one surfactant and at least one active principle wherein said active principle is (are) dissolved in one of said hydrophilic or hydrophobic phases, and in the form of a suspension in the other one of said phases.

Another object of the present invention is to provide a method for producing an impregnated powder allowing to increase the bioavailability and/or the solubility and in particular allowing to increase the absorption, the solubility and/or the protection of the active principle in order to make easier the administration of liposoluble and/or hydrosoluble molecules (generally with a low bioavailability) and wherein the integrity of the active principles is maintained.

Still another object of the present invention is the use of an impregnated powder for increasing the bioavailability and/or the solubility such as previously defined, and more particularly allowing to increase the absorption, the solubility and/or the protection of the active principle in order to make easier the administration of liposoluble and/or hydrosoluble molecules (generally with a low bioavailability), for formulating various preparations.

The above-mentioned objects are reached according to the invention by an impregnated powder for increasing the bioavailability and/or the solubility of at least one active principle comprising a solid inert support, in a particle form impregnated by a liquid medium comprising a hydrophobic phase and optionally a hydrophilic phase, at least one surfactant and at least one active principle dissolved in at least one of said phases, wherein said active principle(s) is(are) also present in at least one of said phases in the form of a suspension.

It is meant herein under "suspension" a dispersion of solid particles in a liquid medium.

Preferably, one of the hydrophobic or hydrophilic phases is in a dispersed form in the other phase.

The liquid medium may moreover optionally comprise one or more co-surfactant(s), or any other builder necessary for preparation, such as a penetration builder, a mucoadhesive agent, a preservative, a dye, a flavouring agent, etc. or mixtures thereof.

Preferably, the phase in which the active principle(s) is(are) dissolved is a saturated solution.

The impregnated powder can be obtained with a method comprising the following steps:
  obtaining a liquid medium comprising a hydrophobic phase, and optionally a hydrophilic phase, at least one surfactant and at least one active principle dissolved in at least one of said phases and present in at least one of said phases in the form of a suspension;
  mixing a suitable amount of the liquid medium and a suitable amount of an inert solid support in a particle form liable to absorb the liquid medium; and recovering an impregnated powder.

Preferably, the dissolved active principle and the active principle in the form of a suspension are located in distinct phases.

In a first embodiment, the liquid medium is obtained by solubilizing an amount of active principle(s) in one of said phases, mixing to the phase containing the active principle(s) dissolved the other one of said phases, adding an additional amount of active principle(s) to the two phase blend so as to form a suspension of the active principle(s).

In another embodiment, the liquid medium is obtained by mixing both phases and adding an amount of active principle(s) sufficient to obtain the dissolution of the active principle(s) in at least one of the phases and a suspension of the active principle(s) in at least one of the other phases.

The active principle(s) may be solubilized or dispersed in the hydrophobic phase or in the hydrophilic phase or in both.

The combination of all these components allows to increase the bioavailability and/or the solubility of the active principle(s).

The method for producing the impregnated powder increasing the bioavailability and/or solubility has the advantage of being easy and cheap to be implemented. All the liquid and powder stirring methods known to the man skilled in the art are useable.

An important feature of the impregnated powder according to the invention is the bioavailability and/or solubility increase of the active principle(s) contained therein.

The impregnated powder for increasing the bioavailability and/or solubility according to the invention may be used as such or included in various formulations.

Thus, another feature of the impregnated powder for increasing the bioavailability and/or solubility according to the invention is to enable the production of various galenical forms, more particularly, deliverable through oral route or mucosal route (oral, nasal, vaginal) or through cutaneous route with a view to a local or systemic action. The galenical forms are generally dry forms such as bare or blistered tablets, sugar-coated tablets, coated tablets (soluble coating, pH-dependent or independent coating, with a gastric, intestinal or other release), matricial tablets, osmotic tablets, multilayered tablets, effervescent tablets, dual core tablets, floating tablets, forms with gastric residence and/or floating forms, mucoadhesive forms, capsules, powders, multiparticle forms such as granules, coated or non coated microgranules (sugar-coated, with a soluble pH-dependent coating), mucoadhesive forms, atomised solids. Such an impregnated powder may also be applied onto fabric-type supports (wipes) to be applied on the body surface, etc.

The resulting galenical forms may have any packaging form.

The impregnated powder for increasing the bioavailability and/or solubility according to the invention has also the advantage of allowing high active material contents. A liquid medium may thus be obtained, saturated or not and dispersed with active material. The so-obtained liquid medium may be impregnated on an inert support.

The following relates to the accompanying drawings showing respectively:

FIGS. 1 to 4 are flowcharts of the main steps of various producing methods of the impregnated powder increasing the bioavailability and/or the solubilization according to the invention; and FIGS. 5 to 8, 10, 11 and 13 are dissolution profiles of the impregnated powder increasing the bioavailability and/or the solubilization according to the invention in comparison with the dissolution profiles of commercial products.

Figure 9:
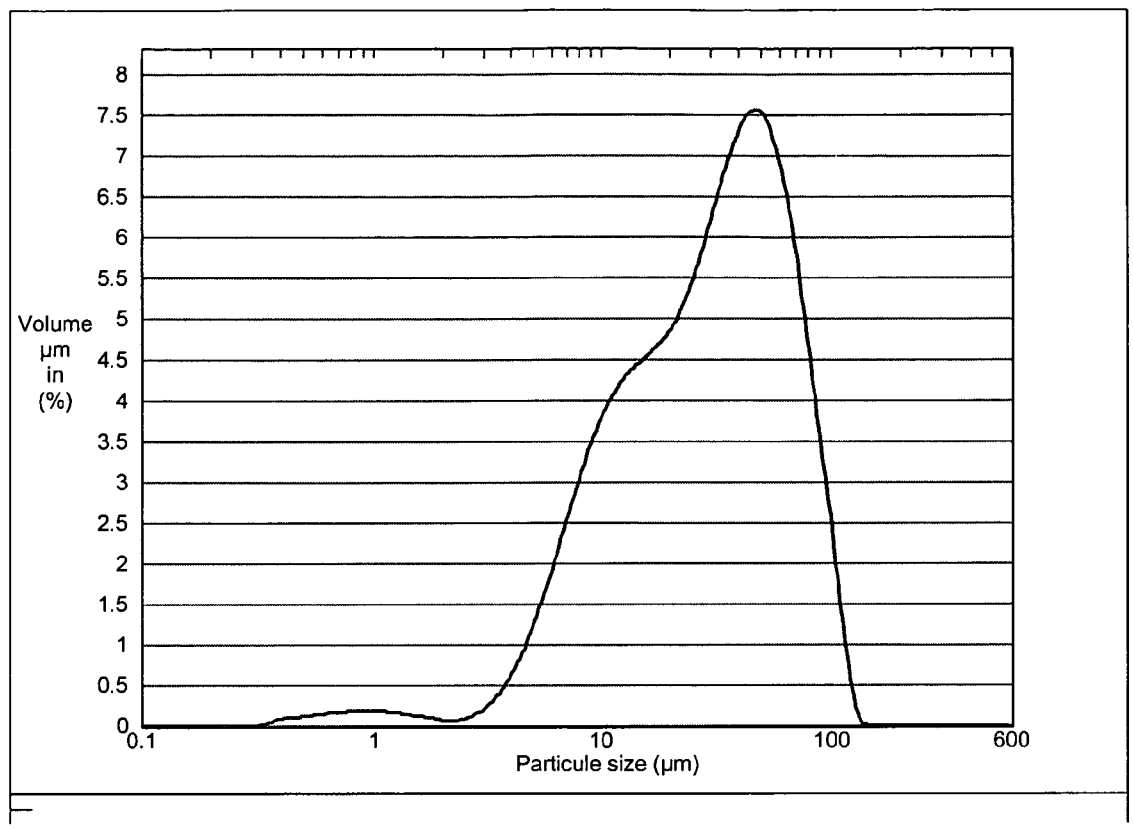
Figure 12:
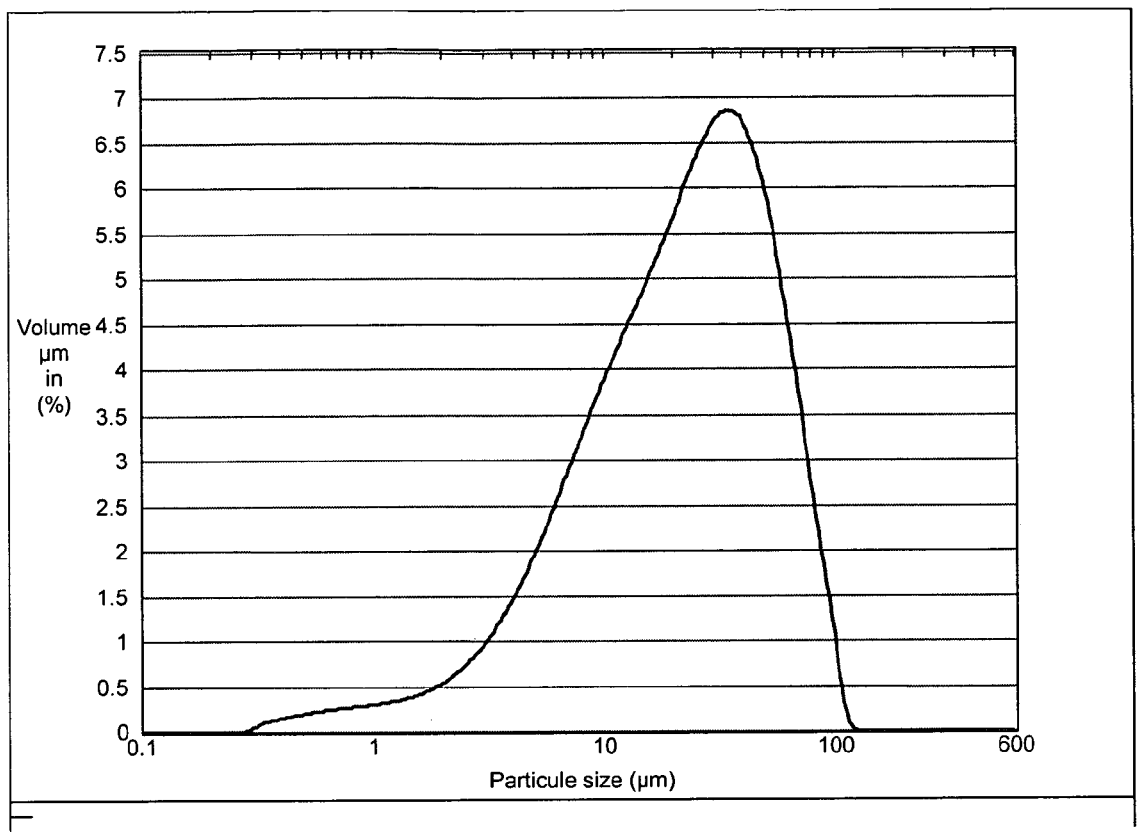

FIGS. 9 and 12 are sieving diagrams of an impregnated powder according to the invention.

The hydrophobic phase of the impregnated powder for increasing the bioavailability and/or solubility may be made of any non toxic compounds conventionally used for forming an oil phase.

In particular, the hydrophobic phase may be selected from vegetable, animal, mineral or synthetic or semi-synthetic oils, mono-, di- or triglycerides, fatty alcohols and any derivatives thereof, polyol esters, liquid paraffin, long chain hydrocarbons such as squalane and squalene, tocopherol and the derivatives thereof, aliphatic fatty acids, fatty acid esters, silicone oils, phospholipid compounds and the derivatives thereof, and mixtures thereof.

The oils making up the oil phase may be polar or apolar oils.

Vegetable oils may include sunflower, olive, soja, corn, sesame, sweet almond, peanut, rapeseed refined oils, as well as avocado, wheatgerm, castor, coconut oils, etc . . . .

Animal oils may include cod-liver oil, shark-liver oil and lanolin oil.

Mineral oils may include paraffin oil.

Fatty alcohols may include behenyl alcohol, cetyl alcohol, isocetyl alcohol, isostearyl alcohol, lauryl alcohol, 2-octyldodecanol, oleyl alcohol, meristyl alcohol and stearyl alcohol.

Aliphatic fatty acids may include isostearic acid, lauric acid, linoleic acid, oleic acid.

Fatty esters may include dibutyl adipate, dibutyl sebacate, dicetyl adipate, diethyl sebacate, dihexyl adipate, diisocetyl adipate, diisopropyl adipate, diisopropyl dimerate, diisopropyl sebacate, diisostearyl adipate, dioctyl adipate, dioctyl sebacate and dioctyl succinate, branched chain fatty esters such as 2-ethylhexyl isononanoate, 2-ethylhexyl myristate, 2-ethylhexyl oxystearate, 2-ethylhexyl palmitate, 2-ethylhexyl pelargonate, 2-ethylhexyl stearate, isocetyl isodecanoate, isocetyl palmitate, isodecyl isononanoate, isononyl isononanoate, isopropyl isostearate, isopropyl laurate, isopropyl linoleate, isopropyl myristate, isopropyl oleate, isopropyl palmitate, isopropyl stearate, isostearyl isostearate, isostearyl lactate, isostearyl neopentanoate, isostearyl palmitate, isopridecyl isononanoate and tocopheryl linoleate, tribasic acid esters such as triisocetyl citrate, triisopropyl trilinoleate, triisostearyl trilinoleate, trilauryl citrate and trioctyl citrate, straight chain fatty esters such as lauryl lactate, lauryl myristate, lauryl palmitate, lauryl stearate, meristyl lactate, myristyl meristate, myristyl neopentanoate, myristyl propionate, myristyl propionate, myristyl stearate, oleyl erucate, oleyl linoleate, oleyl myristate, oleyl oleate, oleyl stearate, stearyl lactate and stearyl oleate.

Triglycerides may include caprylic/capric triglycerides, triisononanoin, triisostearin, trilaurin, trilinolein and triolein.

Silicone oils may include polyorganosiloxane oils, more particularly, polydimethylsiloxane oils, being volatile or non volatile, such as cyclic polydimethylsiloxane oils, having 3 to 6 silicon atoms, for example, cyclomethicone, as well as linear polydimethylsiloxanes.

Generally, the hydrophobic phase is 0.1% to 99.9% by weight, preferably, 5% to 60%, based on the total weight of the liquid medium containing the active principle(s).

The hydrophilic phase of the impregnated powder for increasing the bioavailability and/or solubility may be any aqueous non toxic phase conventionally used by the man skilled in the art.

Thus, the hydrophilic phase may consist in water (distilled or deionised), a hydroalcoholic mixture, in particular a water/alkanol mixture, such as ethanol, a buffered aqueous solution, a saline aqueous solution, a glucosed aqueous solution, and a water-polyethylene glycol, water-propylene glycol and water-glycerol mixture.

Generally, the aqueous phase is 0.1% to 99.9% by weight, preferably 5% to 60% based on the total weight of the liquid medium containing the active principle(s).

As previously indicated, the liquid medium comprising the active principle(s) comprises at least one non toxic surfactant. The surfactant may be non ionic, anionic, cationic or amphiphilic. Such a liquid medium may optionally be neutral or negatively charged, depending on the required functionalities.

(i) Non Ionic Surfactant(s)

The non ionic surfactants are also well known compounds per se (see more particularly "Handbook of Surfactants" by M. R. PORTER, Editions Blackie & Son (Glasgow and London), 1991, pages 116 to 178) and their nature does not show, in the scope of the present invention, any critical feature. Thus, they can be more particularly selected amongst (non limitative list) alcohols, alpha-diols, alkylphenols or polyethoxylated, polypropoxylated or polyglycerolated fatty acids, with one fatty chain comprising for example from 8 to 18 carbon atoms, the propylene oxide or ethylene oxide group number possibly ranging from 2 to 50 and the glycerol group number possibly ranging from 2 to 30. One can also mention the ethylene and propylene oxide copolymers, the ethylene and propylene oxide condensates on fatty alcohols; the polyethoxylated fatty amides preferably having from 2 to 30 ethylene oxide moles, the polyglycerolated fatty amides comprising on average from 1 to 5 glycerol groups and more particularly 1.5 to 4; the oxyethylenated sorbitan fatty acid esters having from 2 to 30 ethylene oxide moles; the saccharose fatty acid esters, the polyethyleneglycol fatty acid esters, the alkylpolyglycosides, the N-alkyl glucamine derivatives, the amine oxides such as the oxides of $(C_{10}$-$C_{14})$ alkyl amines or the N-acylaminopropylmorpholine oxides.

Non ionic surfactants comprise polyoxyethylenated fatty acid esters, saccharose esters, saccharoglycerides, lauryl ethers and derivatives polysorbate, sorbitan ester, dioctylsodium sulfosuccinate, bis-2-ethylhexyl sodium sulfosuccinate and derivatives, all sorbitan derivatives, polyoxyethylene glycol alkyl ether.

(ii) Anionic Surfactant(s)

Their nature does not show, in the scope of the present invention, any really critical feature.

Thus, as an example of useable anionic surfactants, alone or in mixtures, in the scope of the present invention, one may mention amongst others (non limitative list) salts (more particularly alkaline salts, including sodium salts, ammonium salts, amine salts, aminoalcohol salts or alkaline earth (magnesium) salts of the following compounds: alkylsulfates, alkyl-ethersulfates, alkylamidoethersulfates, alkylarylpolyethersulfates, sulphate monoglycerides; alkylsulfonates, alkylphosphates, alkylamido-sulfonates, alkylarylsulfonates, α-olefin-sulfonates, paraffin-sulfonates; alkyl-sulfosuccinates, alkylethersulfosuccinates, alkylamidosulfosuccinates; alkylsulfosuccinamates; alkylsulfoacetates; alkyletherphosphates; acyl-sarcosinates; acylisethionates and N-acyltaurates, the alkyl or acyl moiety of all these various compounds preferably comprising from 12 to 20 carbon atoms, and the aryl moiety preferably representing a phenyl or benzyl group. Anionic surfactants still useable may also include fatty acid salts such as the salts of oleic, ricinoleic, palmitic, stearic acids, coco oil acids or hydrogenated coco oil acids; acyllactylates with an acyl moiety comprising from 8 to 20 carbon atoms. One can also use low anionic surfactants, such as the uronic galactoside D alkyl acids, and the salts thereof, as well as the polyoxyalkylated carboxylic ether $(C_6$-$C_{24})$ alkyl acids, the polyoxyalkylated carboxylic ether aryl $(C_6$-$C_{24})$ alkyl acids, the polyoxyalkylated carboxylic ether amido $(C_6$-$C_{24})$ alkyl acids and the salts thereof, in particular those comprising from 2 to 50 ethylene oxide groups and the mixtures thereof.

Anionic surfactants comprise also petroleum sulfonate, sulfonated glycerides, alpha sulfonate and soaps.

Amongst the anionic surfactants, alkylsulfate salts (for example sodium alkyl sulfate) and alkylethersulfates and the mixtures thereof are preferably used according to the invention.

(iii) Amphoteric Surfactant(s)

The amphoteric surfactants, the nature of which does not show any critical feature in the scope of the present invention, can be more particularly (non limitative list) aliphatic secondary or tertiary amine derivatives, wherein the aliphatic moiety is a linear or branched chain comprising from 8 to 22 carbon atoms and containing at least one hydrosolubilizing anionic group (for example carboxylate, sulfonate, sulfate, phosphate or phosphonate), one can also mention $(C_8$-$C_{20})$alkyl betaines, sulfobetaines, $(C_1$-$C_6)$alkylamidoalkyl $(C_8$-$C_{20})$betaines or $(C_1$-$C_6)$alkylamidoalkyl $(C_8$-$C_{20})$sulfobetaines.

Amphoteric surfactants comprise also synthetic, semi synthetic, natural modified, natural phospholipides with grafts (licithin, phosphatidylcholine, phosphatidylethanolamine, phosphatidylinositol, phosphatidylserine, phytoglycolipide, lysophosphatide, sphyngomyeline), alkylaminocarboxylic acids.

(iv) Cationic Surfactant(s)

The cationic surfactants, the nature of which does not show any critical feature in the scope of the present invention, can be more particularly (non limitative list) alkylated quaternary ammonium, alkylamine salts and amine oxides.

Cationic surfactants comprise cetrimide, primary amines, fatty amine acetate and chlorhydrate, quaternary ammonium salts, substituted diamine amides and derivatives, diethylene triamine amides.

Generally, the amount of surfactant present is of at least 1% by weight based on the total weight of the liquid medium, generally from 2% to 70% by weight and preferably from 10% to 60% by weight.

Preferably, the liquid medium also contains at least one co-surfactant. The co-surfactant is a compound with its molecule generally considerably smaller than that of the surfactant and the role thereof is to act on the molecular stack at the droplet interface, such that the liquid medium formation is energetically favoured.

Preferred co-surfactants may include (non limitative list) alkanols, more particularly $C_3$ to $C_6$ alkanols, glycol ethers, glycol and the derivatives thereof, propylene glycol and the derivatives thereof, lauric esters of propylene glycol, polyglycerol and the derivatives thereof, oleic esters of polyglycerol and ethyldiglycol.

Co-surfactants comprise polyoxylated castor oil, hydrogenated polyoxylated castor oil, polyglyceryl and derivatives, organic acids (oleic acid, naphtalenic acid, resin acid, diacidalcohols (tartric acid . . . ) triacid-alcohols (citric acid), diacids (malonic acid, maleic acid, succinic acid, adipic acid), hydrophile and/or lipophile alcohols (methanol, ethanol, propanol, isopropanol, butanol, isobutanol, pentanol, isoamylic alcohol, hexanol, heptanol, octanol . . . ) hydrophile and/or hydrophobe glycols (ethylene glycol, propylene glycol, isopropylene glycol, butylene glycol, 2-3 butanediol, isobutene glycol, 2-4 butanediol, hexylene glycol . . . ) fatty acids and the derivatives thereof (lauric acid, palmitic acid, oleic acid, stearic acid), polyols (glycerol, trimethylolpropane, 2-3-4-pentanetriol) amines and polyamines and the derivatives thereof (dimethylamine, ethylene diamine, diethylene triamine, triethylene tetramine, tetra ethylene pentamine . . . ), amino-alcohols (ethanolamine, diethanolamine, triethanolamine, diethyl amino ethanol . . . ).

The co-surfactant, when used, generally is 0.01% to 60% by weight based on the total weight of the liquid medium containing at least one active principle.

The active material(s) included in the liquid medium may be any active principle with an activity in the pharmaceutical, parapharmaceutical and cosmetic field, in the field of food complements or in the food processing industry, in particular in the cosmetic and/or therapeutic fields, preferably the therapeutic one. Such active principles may be soluble and/or dispersible in one or the other of the liquid medium components. In particular, the active principles can be hydrosoluble, liposoluble or amphiphilic.

The active principles from chemical, natural or biological origin, used according to the invention may be selected amongst those conventionally used in the following pharmacotherapeutic families: allergology, anesthesia/resuscitation, cancerology and hematology, cardiology and angiology, contraception and pregnancy interruption, dermatology, endocrinology, gastro-entero-hepathology, gynecology and obstetrics, immunology and transplantation drugs, infectiology and parasitology, diabetes metabolism and nutrition, neurology/psychiatry, ophthalmology, otorhinolaryngology, pneumology, rhumatology, stomatology, toxicology, urology/nephrology, as well as amongst analgesics/antipyretics and antispasmodics, anti-inflammatory drugs, contrast products used in radiology, haemostatics and blood treatment products and derivatives.

Advantageously, the active principles may be selected amongst the group comprising active principles passing the mucosal barrier and reaching the systemic circulation, such as cyproterone acetate, $\Delta$-4-androstenedione, 3-keto-desogestrel, desogestrel, gestodene, estradiol and the derivatives thereof, norethisterone acetate, progesterone, testosterone, dihydro-testosterone, trinitrine, fentanyl, nitroglycerin, nicotine (S(−) nicotine), scopolamine, clonidine, isosorbide dinitrate, levonorgestrel in combination with ethinylestradiol or with estradiol, androstanolone, alclometasone dipropionate, phlorglucinol, molsidomin, as well as their combinations.

They may also be selected amongst the active principles passing the mucosal barrier and having a localized action such as: acetazolamide, acyclovir, adapalene, alclometasone dipropionate, amcinonide, ameleine, bamethan sulphate+escin, betamethasone valerate, betamethasone dipropionate, bufexamac, cafein, calcipotriol monohydrate, cetrimonium bromide, clobetasol propionate, crilanomer, desonide, dexpanthenol, diclofenac, diflucortonole valerate, difluprednate, diphenydramine hydrochloride, econazole nitrate, erythromicin, flumetasone pivalate, fluocinolone acetonide, fluocinodin, fluocortolone, fluocortolone hexanoate, fluocortolone pivalate, hydrocortisone, hydrocortisone acetate, ibacitabin, ibuprofen, imiquimod, ketoconazole, ketoprofen, lidocaine, metronidazole, miconazole nitrate, minoxidil, acidic niflumide, penciclovir, benzoyl peroxide, piroxam, iodized povidone, promestriene, pyrazonibutasone, roxithromycin, sulfacetalmide, triamsinolone, tazarotene, tretinoin and isotretinoin, triclocarban, vidarabin monophosphate, as well as their combinations.

They may also be selected amongst the following active principles: adrenergic β-3 agonist, growth hormone, oxibutinin, buprenorphin, pergolid, nestoron, 7 α-methyl-19-nortesterone, mecamylamin, salbutamol, selegilin, buspirone, ketotifen, lidocain, ketorolac; eptazocin, insulin, α-interferon, prostaglandins, 5-aminolevulinic acid, benzodiazepine alprozolam, diclofenac, fenoprofen, flubiprofen, ketoprofen, methylphenidate, miconazole, piroxicam, buprenorphin, alprozolam, dexmedetomidin, prazosin (α-adrenergic antagonist), alprostadil, tulobuterol (β-adrenergic agonist), thinylestradiol+norelgestromin, ketorolac, physostigmin, medindolol (β-adrenergic agonist), rotigotin, (D2 dopamin antagonist), thiatolserin as well as their combinations.

They may also be selected amongst the following active principles Esomeprazole, Melagatran (in case of thrombosis), Rosuvastatine, Ezetimide, Pitavastatine (hyperlipidemia), Mitiglinide (type II diabetes), Cilomilast, Viozan (asthma), Aripipazole (psychiatry), Omapatrilat (hypertensor), Orzel (cancerology), Capspofongine acetate, Voriconazole (infections), new COX inhibitors such as Etoricoxib (inflammation), Valdecoxib (arthritis) and Parecoxib, P-antagonist substance (depression), Darifenacin (urology), Eletriptan (migrain), Alosetron, Tegaserod, Capravirin (HIV) as well as their combinations.

Preferred active principles according to the invention may include vitamin A derivatives (for example isotretinoin, coenzyme Q10), antiviral agents (for example acyclovir), analgesics (for example indometacin, naproxene), anti-ulcer agents (for example omeprazole, lansoprazole), antimoulds (for example Cyclosporin), antibiotics (cefaclor, amoxicillin, cloxacilin), sex hormones (antiestrogenes, for example raloxifene; estrogenes, for example estradiol, estradiol hexahydrobenzoate, estradiol undecylate, estradiol valerate, estradiol ethinyl; progestins, for example norethisterone enanthate, progesterone; androgens, for example testosterone propionate, testoterone cyclohexylmethylcarbonate, and antiandrogens, for example cyproterone acetate.

The active principles may be also selected amongst those conventionally used in cosmetics, parapharmacy and for food complements. Such active principle contents are those conventionally used in the mentioned fields.

Cosmetic and parapharmaceutical active principles may include emollients, wetting agents, pigments and dyes, anti-wrinkle agents (retinol), anti-fungal agents, anti-acne agents, softening agents, perfumes and vitamins.

Actives for food complements may include vitamins (A, B, E, C, B1, B2, B3, B6, B9, B12, B8H, B5, . . . ), minerals (calcium, phosphorus, iron, magnesium, zinc, iodine, . . . ), carotenoids (alpha-caroten, beta-caroten, gamma-caroten, lutein, zeaxanthin, cryptoxanthin, lycopene, . . . ), phytoestrogens, isoflavones (genistein, diadzein, biochanin A, formononetin, . . . ), lignans (enterolactone, enterodiol, . . . ), coumestanes (coumestrol), vegetable extracts (fennel, heather, blackcurrant, grape seed extracts, fucus, ginseng, green coffee, ginger, . . . ), oils (oenothera, wheatgerm, borage, marrow seeds, . . . ), clays (diosmestite-montmorillonites, . . . ), ferments and yeasts, as well as apple pectin.

Depending on the selected active principle (or the active principle mixture), several liquid medium formulations are available depending on the desired release profile.

Generally, the active material content of the impregnated powder for increasing the bioavailability and/or the solubility according to the invention ranges from 0.001% to 70% by weight, preferably 0.5% to 60% by weight, based on the liquid medium total weight, depending on the active material nature.

The liquid medium may also contain a penetration builder or a mixture of builders intended to improve the passage of the active molecules through the involved membrane. Penetration builders may include those which may be selected in the group consisting of aliphatic fatty acid esters such as the isopropyl myristate, fatty acids such as oleic acid; alcohols or polyols such as ethanol, propylene glycol and polyethylene glycol; essential oil and terpene derivatives components (such as eugenol, geraniol, nerol, eucalyptol, menthol); preferably non ionic surfactants, such as polyoxyethylene sorbitan (fatty acid ester), polyoxyethylene alkyl ether, polyoxyethylene derived from castor oil, as well as their mixtures; hydrating agents such as glycerin, urea; keratolytic agents such as alphahydroxyacids, 23-lauryl ether, aprotinin, nitrogen, benzalkonium chloride, cetylpyridinium chloride, cetyltrimethylammonium bromide, cyclodextrins, dextran sulfate, lauric acid, lysophosphadidylcholine, methoxysalicylate, methyloleate, oleic acid, phosphatidylcholine, polyoxyethylene, polysorbate 80, sodium EDTA, sodium glycocholate, sodium glycodeoxycholate, sodium lauryl sulfate, sodium salycilate, sodium taurocholate, sodium taurodeoxycholate, sulfoxides and alkyl glycosides.

The liquid medium may also comprise an adhesive agent (mucous membrane, skin) so as to obtain finally an impregnated powder increasing the bioavailability and/or the bioadhesive solubility. Adhesive agents may include carbomers, polyoxyethylenes, methylcelluloses, carboxymethyl-celluloses, sodium carboxymethylcelluloses, hydroxyethylcelluloses, hydroxypropylcelluloses, hydroxypropylmethylcelluloses, polyvinyl-pyrrolidone, polyvinyl alcohol, polyisobutylene, polyisoprene, xanthane gum, locust bean gum, chitosan, polycarboxylates, acrylic/methacrylic acid copolymers, acrylic acid/acrylamide copolymers, acrylic acid/methylmethacrylate copolymers, acrylic acid/polyethylene glycol copolymers, polyacrylic acid/butyl acrylate copolymers, 2-hydroxy-ethylmethacrylate (HEMA), the compound commercialized under the trademark CYDOT® by 3M corporation (carbopol associated with polyisobutylene), (low viscosity) pectin, methylvinylether/maleic anhydride copolymers, tragacanth, monoethylether, monomethylether, waxy corn starch, sodium stearyl fumarate, sodium hyaluronate, guar gum, sodium alginate, starch, dextran and the derivatives thereof, acrylic polymers, silicones and siliconed derivatives, colophan resins and the mixtures thereof.

Generally, the amount of adhesive agents present in the liquid medium is 0.01% to 70% by weight based on the total weight of the liquid medium.

It may also be interesting to introduce into the liquid medium one or more thermoreversible polymers such as the compounds available under the trademarks LUTROL® and XULOGLUCAN®, in particular for administration through mucosal or cutaneous route. Thus, the impregnated powder according to the invention may be gelled by contact with the mucous membrane or the epiderm. Generally, such polymers are present in an amount ranging from 0.01% to 70% by weight based on the total weight of the liquid medium.

The invention has also the advantage to allow for high active principle contents.

The liquid medium is generally 1% to 99%, preferably 20% to 90%, more preferably 40% to 90%, and more preferably 50% to 80%, based on the total weight of the impregnated powder increasing the bioavailability and/or the solubility.

The inert support in a particle form may be any non toxic support, chemically inert relative to the liquid medium containing the active principle and to its constituents, suitable for the contemplated application and able to be impregnated by the liquid medium without damaging the integrity thereof.

These are generally non toxic inert powders having a strong adsorbing power, liable to adsorb several times their own weight in liquid.

The suitable particle inert supports may include natural silicas, silica gels, fumed silicas, precipitated silicas, clays, talc, magnesium hydroxide, aluminum hydroxide, magnesium oxide, maltodextrins, cyclodextrins, some cellulose derivatives such as cellulose powder and the mixtures thereof.

The preferred particle inert supports are the silicas. The silicas may be hydrophilic, hydrophobic or amphiphilic. Suitable silicas are available under the trademarks AEROSIL® (hydrophilic, hydrophobic), AEROPERL® (hydrophilic, hydrophobic), SYLOID® and SIPERNAT® (amphiphilic).

Amongst the clays, one can mention montmorillonites and bentonites.

Maltodextrins are available under the trademark LYCATAB®.

The particle mean size of particle inert supports according to the invention generally ranges from 0.001 to 300 µm, preferably from 1 to 100 µm.

Generally, the particle inert support is 1% to 90%, preferably 10% to 80%, more preferably 10% to 60%, most preferably 20% to 50% by weight based on the total weight of the impregnated powder increasing the bioavailability and/or the solubility.

The impregnated powder may generally comprise any other builder necessary for the preparation such as (non limitative list) flavoring agents, perfumes, essential oils, dyes, antioxidants, preservatives, sweeteners, fillers, etc. or the mixture thereof.

Generally, the particle size of the impregnated powder for increasing the bioavailability and/or the solubility according to the invention ranges from 1 to 100 µm, preferably from 20 to 50 µm.

The impregnated powder for increasing the bioavailability and/or the solubility according to the invention may easily be produced through the following general mode: first a liquid medium is produced, containing at least one active principle in a form both dissolved and in the form of a suspension. The liquid medium containing at least one active principle is progressively impregnated under stirring on the particle inert support. After homogenization of the mixture, the formulation is recovered in the form of an impregnated powder for increasing the bioavailability and/or the solubility.

FIGS. 1 to 4 show block diagrams of the main steps of alternative production methods for the impregnated powder for increasing the bioavailability and/or the solubility according to the invention.

Referring to FIG. 1, it is shown the main production steps of an impregnated powder for increasing the bioavailability and/or the solubility according to the invention comprising a hydrophobic active principle.

As shown in FIG. 1, first all the components with a lipophilic nature are mixed (the hydrophobic medium, the surfactants and optionally the co-surfactant), followed by a solubilization of the hydrophobic active principle, under stirring, in this hydrophobic medium. In order to have the maximum thermodynamic activity, the active principle is solubilized up to saturation, but the case where it is not up to saturation can be contemplated.

After solubilization of the hydrophobic active principle, the aqueous medium is introduced under stirring. A liquid is obtained containing the active principle(s) up to saturation or not depending on the case. At this stage, an additional amount of the hydrophobic active principle is added, under stirring, until the desired active principle content is obtained. A suspension is thereby obtained, generally in a creamy and opaque semi-solid form.

Such a suspension is then impregnated on the inert solid support under simple stirring. The impregnated powder for increasing the bioavailability is thereby obtained.

Figure 2:
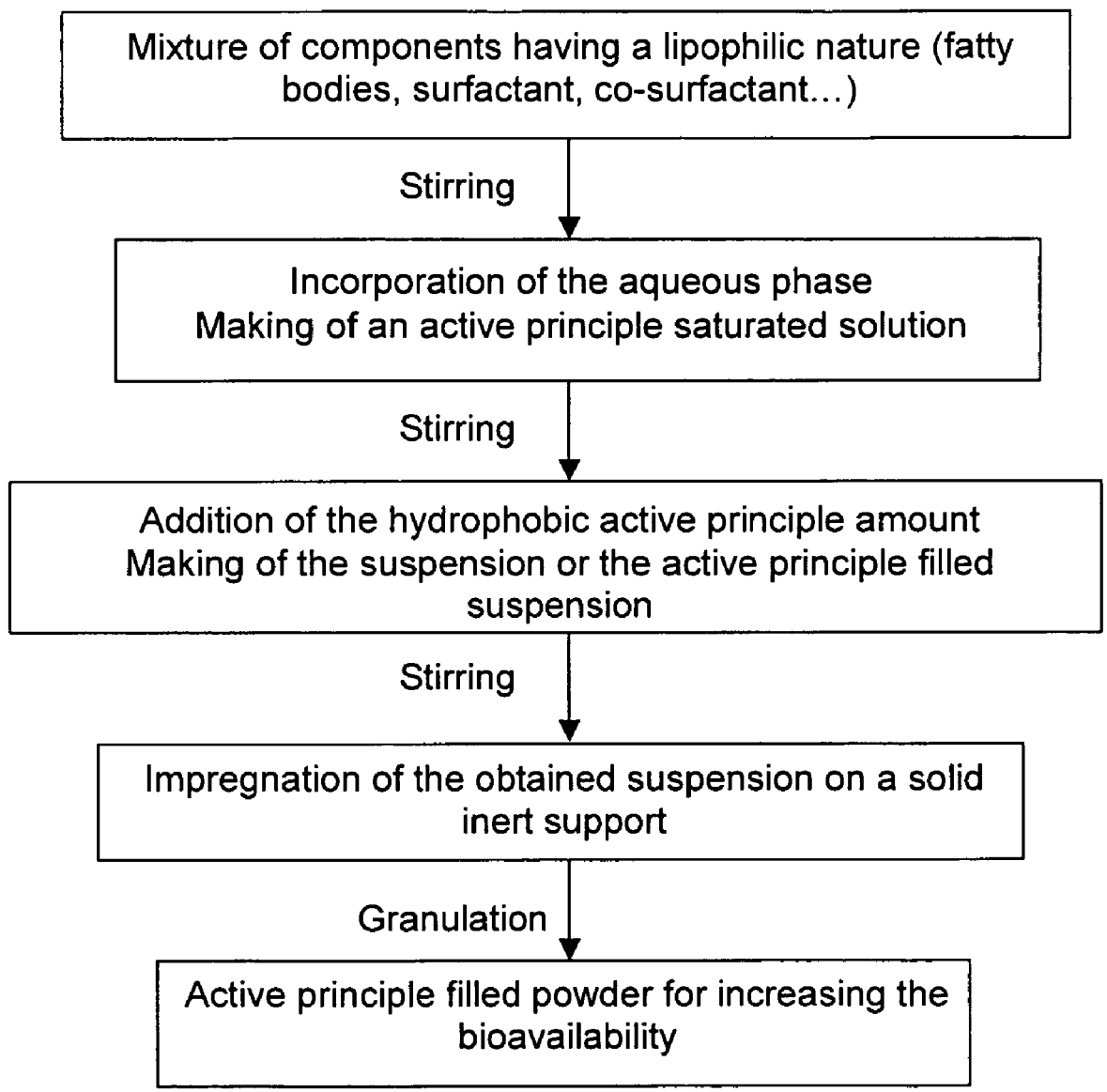

FIG. 2 relates to an alternative of the method in FIG. 1 which differs from the latter in that the hydrophilic medium is first added under stirring to the hydrophobic medium, followed by the addition, under stirring, of the desired amount of hydrophobic active principle until the suspension is obtained. The desired active principle amount can thus be obtained. As in the previous case, the suspension is then impregnated on the inert support with a simple stirring.

Figure 3:
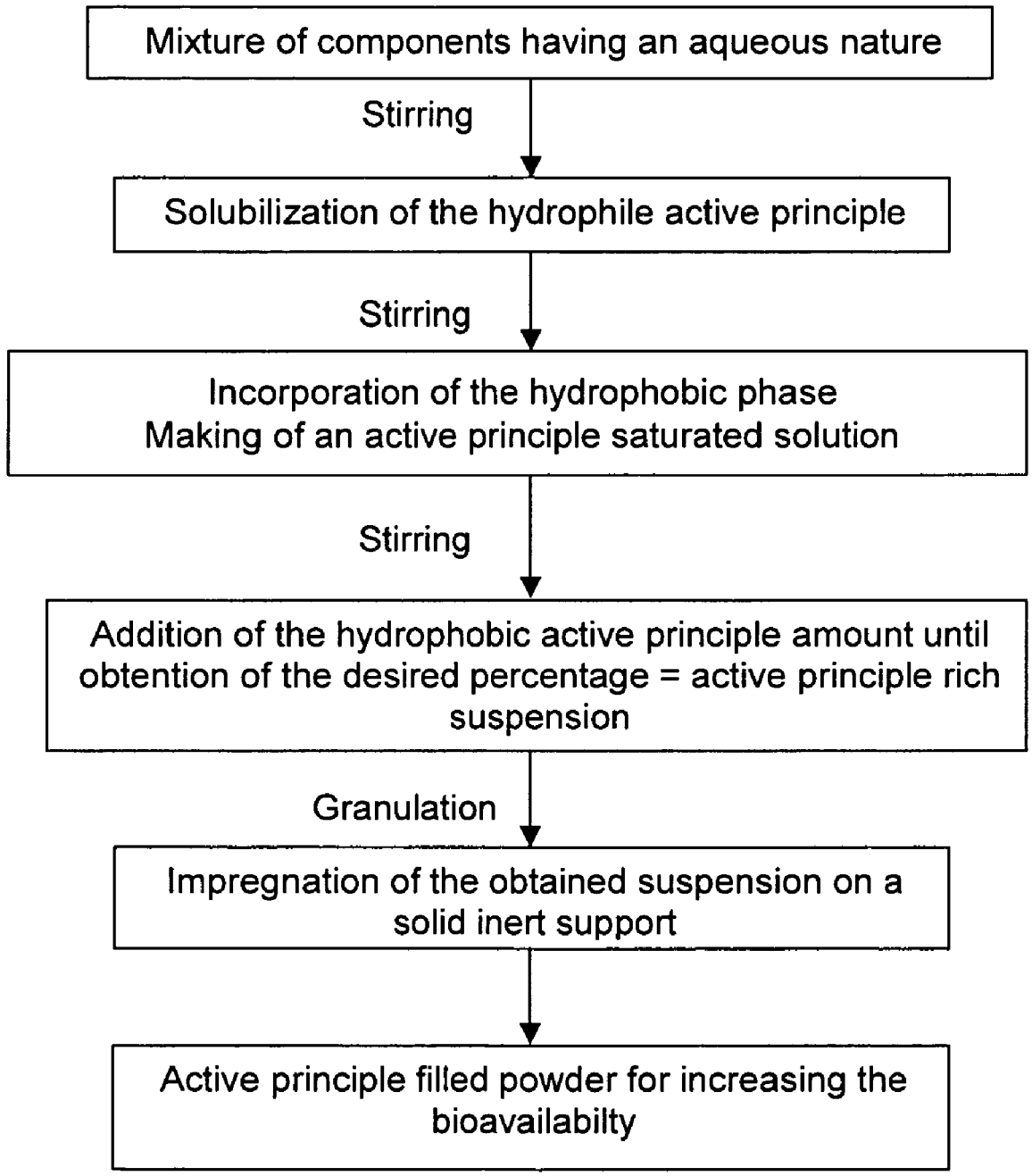
Figure 4:
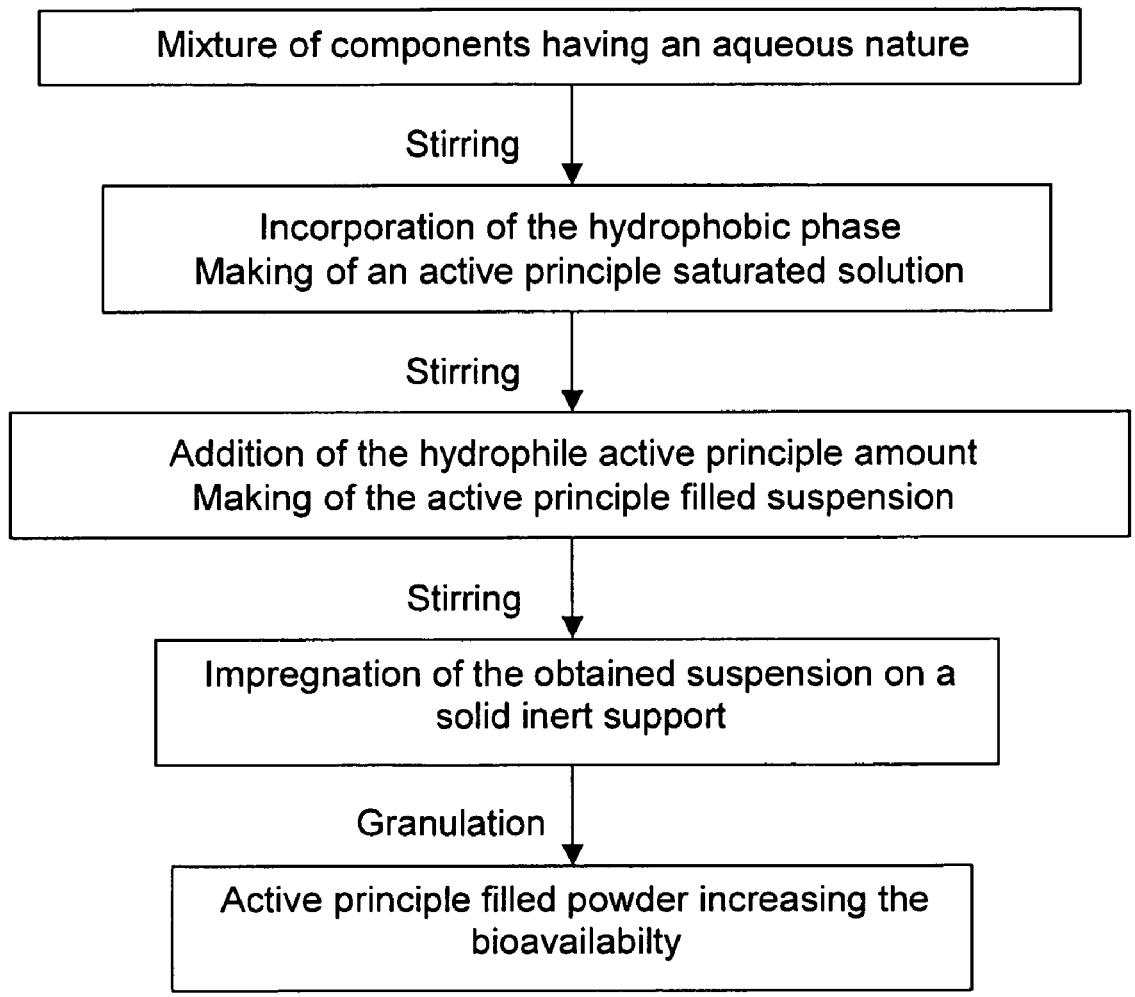

The methods in FIGS. 3 and 4 are similar to those in FIGS. 1 and 2 respectively, but relate to the incorporation of a hydrophilic active principle, and for which the preparation and incorporation order of hydrophobic medium and the aqueous medium has been inverted.

As previously indicated, the impregnated powder for increasing the bioavailability and/or the solubility according to the invention may be used for preparing various forms, in particular galenical forms to be administrated through oral or mucosal route, as well as forms used in cosmetic industry, food complements, food processing industry and parapharmaceutical industry.

In the case of an amphiphilic active principle, the making method remains similar to those previously described.

The impregnated powder for increasing the bioavailability and/or the solubility may also be used alone as such and in various forms in (non limitative list of the invention) bags, stick-packs, pressurized or non pressurized flasks with or without applicators, wipes, etc.

According to the composition of the liquid medium, the impregnation support selected amongst inert powders, the selected galenical form, various release profiles are then available such as an immediate, modified, delayed, bimodal, pulsed release.

The impregnated powder for increasing the bioavailability of the invention may also be converted into capsules, stick packs (and remain in a powder form), bags, powder sprays for nasal, oral or vaginal route, powder sprays with special applicators, etc.

In order to obtain a tablet, it is just sufficient to add one or more diluents (for example, microcrystalline cellulose, lactose, cellulose powder, dicalcium phosphate, sucrose, starch, bicarbonate, mannitol, . . . ), lubricants (for example magnesium stearate, sodium stearyl fumarate, . . . ), binders (for example polyvinylpyrrolidone-vinyl acetate copolymer, povidone, . . . ), disintegration agents (starch and derivatives, sodium starch glycolate, alginate, microcrystalline cellulose, sodium croscarmellose, crosspovidone, . . . ) or others excipients needed for producing tablets.

The tablets may be obtained through direct compression, wet route granulation, dry route granulation or any other techniques known to the man skilled in the art.

It is possible to make multilayered or dual-core tablets, coated tablets (enteric coatings, taste-concealing coating), effervescent tablets, gastric residence or floating tablets.

EXAMPLE 1

Production of Quick Release Progesterone Based Tablet

Active Principle Saturated Solution, Solution A

The sunflower oil based solution (Lesieur) is progesterone saturated. The surfactant/co-surfactant ratio is set at 75/25. A mixture of Tween® 80 (Seppic) and Montane® 80 (Seppic) is used. The co-surfactant is the Transcutol® P (Gattefossé), it also plays the part of an absorption promotor and improves the passage through the mucous membrane.

| Components | Formulation (% w/w) |
|---|---|
| Sunflower oil | 34.09 |
| Montane 80 | 33.65 |
| Tween 80 | 9.62 |
| Transcutol P | 14.42 |
| Micronized progesterone | 4.37 |
| Distilled water | 3.85 |

The sunflower oil, the Montane® 80, the Tween® 80 and the Transcutol® P are thus mixed using a Heidolph Bioblock RZR2051 stirrer at 500 rpm for 6 minutes.

A translucent phase is obtained into which the progesterone is incorporated so as to saturate the mixture. At room temperature, under mechanical stirring with the Bioblock Heidolph RZR 2051 stirrer at 700 rpm for 4 minutes, it is possible to place the solution in an ultra-sound bath for a few minutes (6 minutes 30 seconds) in order to accelerate the solubilization process of the active principle.

Once the active principle dissolved, water is added. The mixture is homogenized with a Bioblock Heidolph RZR 2051 stirrer at 500 rpm for 5 minutes.

A solution A is thereby obtained, which is saturated with clear yellowish transparent and liquid progesterone.

Progesterone Suspension Obtained with Solution A: Suspension B

Progesterone is added at 62.5% by weight of the previous solution so as to obtain an active principle 40% dosed suspension. With a view to this, the progesterone is added in the solution A under mechanical stirring with the Bioblock Heidolph RZR 2051 stirrer at 700 rpm for 5 minutes.

Such suspension B, which is generally a creamy and opaque semi-solid form, has the following composition:

| Components | Formulation (% w/w) |
|---|---|
| Sunflower oil | 21.31 |
| Montane 80 | 21.03 |
| Tween 80 | 6.01 |
| Transcutol P | 9.01 |
| Micronized progesterone | 40.23 |
| Distilled water | 2.41 |

The resulting mixture is a white opaque and thick cream.

Suspension B Impregnation on an Inert Support

Once said suspension B is obtained, it is impregnated on silica such as Sipemat®50 (Degussa). For this handling, a Zanchetta mixer-granulator-dryer is used.

Parameters:

Paddle speed: 300 rpm

Suspension introduction time=20 minutes

Homogenization time=7 minutes

The progesterone suspension B is progressively incorporated into the device so as to be impregnated on the silica.

The impregnated powder increasing the bioavailability and/or the solubility has then the following composition:

| Components | Formulation (% w/w) |
| --- | --- |
| Sunflower oil | 16.41 |
| Montane 80 | 16.2 |
| Tween 80 | 4.63 |
| Transcutol P | 6.94 |
| Micronized progesterone | 30.97 |
| Distilled water | 1.85 |
| Sipernat 50 | 23 |

Dissolution Profile of the Impregnated Powder for Increasing the Bioavailability and/or the Solubility, as Defined Above, Compared to a Commercially Available Pharmaceutical Form: Utrogestan® 100 Mg (Besins)

The in-vitro dissolution test has been made with an AT7 Sotax dissolutest with glass dissolution beakers. The dissolution medium being used is 1% kleptose. The bath temperature is maintained at 37° C. and the paddle rotation speed is 150 rpm.

The dosage occurs on line through UV spectrometry.

Figure 5:
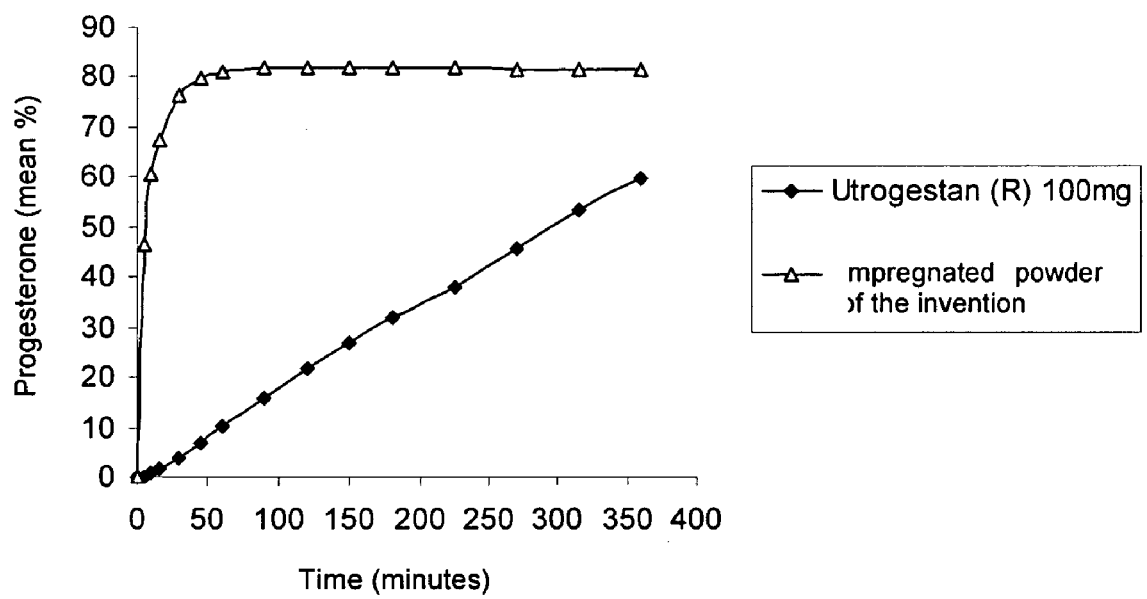

The results are schematically represented in FIG. 5.

The whole dose is released within one hour with the impregnated powder for increasing the bioavailability of the invention, whereas the commercial formulation hardly releases more than 50% within 6 hours.

Characterization of the Impregnated Powder for Increasing the Bioavailability and/or the Solubility of the Invention Pouring Ability This test is performed according to the European Pharmacopoeia test 4.2, 2.9.16.
Sample mass=63.42 g
Pouring time=infinite Bulk Volume This test is performed according to the European Pharmacopoeia test 4.2, 2.9.15.
Sample mass=64 g
Bulk volume at V0=122 ml
Bulk volume at V10=114 ml
Bulk volume at V500=104 ml
Settling ability=10 ml Measurement of the Relative Humidity Rate This measure is made using a Sartorius MA 30 humidity analyzer.
Parameters: sample mass=1.69 g,
Temperature=100° C.
Drying time=15 min
Result: relative humidity=9.70%

Granulometry

This study is performed using a Mastersizer 2000 Malvern laser granulometer provided with a Sirocco 2000 vibrator.
Parameters: pressure=2 bars, 70% vibration
Mean granulometry=27.5 μm Tablet Production The diluent being used is a mixture of Vivapur® 102 (Rettenmaïer) and Encompress® (Penwest).

With the Turbula mixer, the diluents and the impregnated powder are mixed for 5 minutes. With the help of an alternative pressing machine, with 11R11 stamps, tablets are produced comprising 20% of the previous blend.

The tablet composition is as follows:

| Components | Formulation (% w/w) |
| --- | --- |
| Previous blend | 20 |
| Vivapur 102 | 40 |
| Encompress | 40 |

Tablet Features
mass=460 mg
hardness=40 N
desagregation=20 seconds

EXAMPLE 2

Production of a Quick Release Fenofibrate Based Impregnated Powder for Increasing the Bioavailability and/or the Solubility The A1 suspension is made based on Labrafac® CC (Gattefossé), Montanox® 85 (Seppic), propylene glycol (Copper) and distilled water. The first three components are mixed using a Bioblock Heidolph RZR 2051 stirrer at 700 rpm.

Then, the distilled water is added and a mechanical stirring is made with a Bioblock Heidolph RZR 2051 stirrer at 700 rpm.

The active principle is added to the previous blend, the formulation is sent through an ultra-sound bath for 5 minutes, and then subjected to a mechanical stirring carried out with a Bioblock at 1200 rpm for 45 minutes.

The formulation is as follows:

| Raw materials | Formulation (% w/w) |
| --- | --- |
| Labrafac CC | 35.49 |
| Montanox 85 | 33.92 |
| Propylene glycol | 3.95 |
| Fenofibrate | 23.6 |
| Distilled water | 3.04 |

A rather thick white solution is obtained.

Fenofibrate-filled Suspension A1 Impregnation

Once said suspension is obtained, it is impregnated on silica such as Sipernat® 50 (Degussa). For this handling, a Zanchetta mixer-granulator-dryer is used.

Parameters:
Paddle speed=300 rpm
Suspension introduction time=20 minutes
Homogenization time=7 minutes

| Raw materials | Formulation (% w/w) |
| --- | --- |
| Suspension A1 | 69 |
| Sipernat 50 | 31 |

The fenofibrate-filled formulation is progressively incorporated into the device so as to be impregnated on the silica.

Dissolution Profile of the Impregnated Powder for Increasing the Bioavailability and/or the Solubility, as Defined Above, Compared to a Commercially Available Pharmaceutical Form: Lipanthyl® 160 mg.

The in-vitro dissolution test has been made with an AT7 Sotax dissolutest, with rotating paddles. The dissolution medium being used is 0.1M SLS. The bath temperature is maintained at 37° C. and the paddle rotation speed is 75 rpm.

Figure 6:
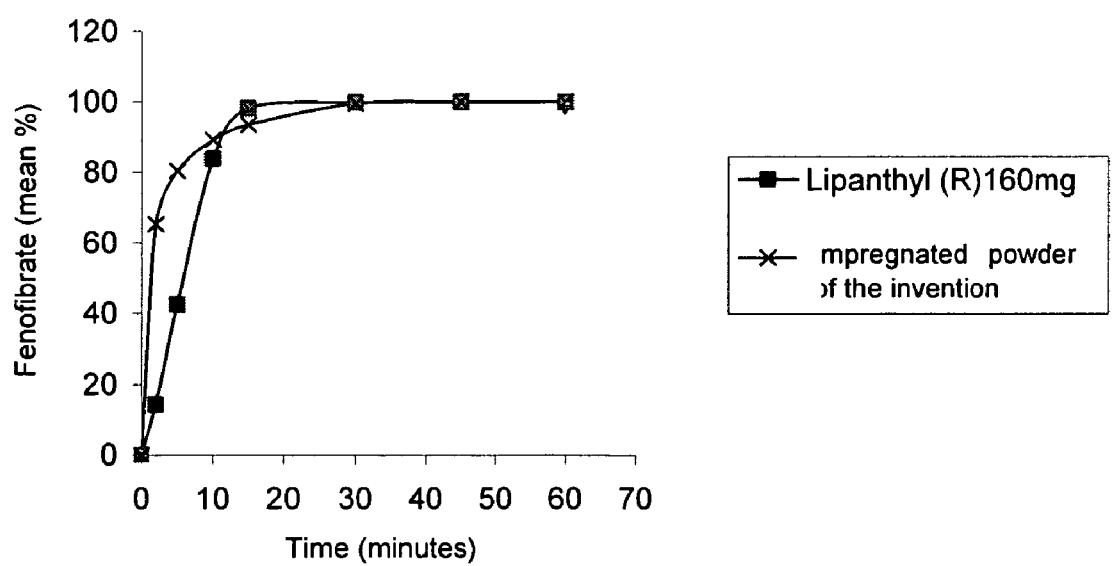

The dosage occurs on line through UV spectrometry. The results are schematically represented in FIG. 6.

The impregnated powder for increasing the bioavailability and/or the solubility of the invention makes it possible to release active principle much faster than the Lipanthyl® 160 mg during the first 10 minutes.

Characterization of the Impregnated Powder for Increasing the Bioavailability and/or the Solubility of the Invention Pouring Ability This test is performed according to the European Pharmacopeia test 4.2; 2.9.16.
Sample mass=65.64 g
Pouring time=infinite Bulk Volume This test is performed according to the European Pharmacopeia test 4.2; 2.9.15.
Sample mass=65.64 g
Bulk volume at V0=154 ml
Bulk volume at V10=148 ml
Bulk volume at V500=128 ml
Bulk volume at V500=126 ml
Settling ability=20 ml Measurement of the Relative Humidity Rate This measure is made using a Sartorius MA 30 humidity analyzer.
Parameters: sample mass=1.002 g,
Temperature=100° C.

Drying time=15 min
Result: relative humidity=5.69%

Granulometry

This study is performed using a Mastersizer 2000 Malvern laser granulometer provided with a Sirocco 2000 vibrator
Parameters: pressure=2 bars, 70% vibration
Mean granulometry=20.89 μm

EXAMPLE 3

Production of a Quick Release Acyclovir Based Impregnated Powder for Increasing the Bioavailability and/or the Solubility The A2 suspension is produced from a HCl aqueous solution at pH 2, refined soja oil (Sictia), Tween® 80 (Fluka), propylene glycol (Cooper). The last three components are mixed using a Bioblock Heidolph RZR 2051 stirrer at 500 rpm.

Then, the HCl aqueous solution at pH 2 is added, under mechanical stirring, with a Bioblock Heidolph RZR 2051 stirrer at 700 rpm.

The active principle is added to the previous blend, the formulation is sent through an ultra-sound bath for 5 minutes, and then followed by a mechanical stirring with the Bioblock at 900 rpm for 20 minutes.

The formulation is as follows:

| Raw materials | Formulation (% w/w) |
|---|---|
| Refined soja oil | 5.49 |
| Tween 80 | 44.49 |
| Propylene glycol | 4.95 |

| Raw materials | Formulation (% w/w) |
|---|---|
| Acyclovir | 23.07 |
| HCl aqueous solution at pH 2 | 22 |

A rather thick white solution is obtained.

Acyclovir-filled A2 Suspension Impregnation

Once said suspension is obtained, it is impregnated on silica, such as Aeroperl®300 (Degussa). For this handling, a Zanchetta mixer-granulator-dryer is used.

Parameters:
Paddle speed=350 rpm
Suspension introduction time=25 minutes
Homogenization time=9 minutes The acyclovir-filled formulation is progressively incorporated into the device so as to be impregnated on the silica.

The resulting impregnated powder formulation for increasing the bioavailability and/or the solubility is as follows:

| Raw materials | Formulation (% w/w) |
|---|---|
| Suspension A2 | 69 |
| Sipernat 50 | 31 |

EXAMPLE 4

Production of Quick Release Progesterone Based Tablet.

Active principle saturated solution, solution A.

The sunflower oil based hydrophobe phase (Lesieur) is progesterone saturated. The surfactant/co-surfactant ratio is set at 75/25 A mixture of Tween® 80 (Seppic) and Montane® 80 (Seppic) is used. The co-surfactant is the Transcutol® (Gattefossé), it also plays the part of an absorption promotor and improves the passage through the gastrointestinal mucous membrane.

| Components | % w/w |
|---|---|
| Refined Sun flower oil | 36.61 |
| Montane 8O | 32.02 |
| Tween 8O | 9.14 |
| Transcutol HP | 13.73 |
| Progesterone | 4.37 |
| Purified water | 4.13 |

The sunflower oil, the Montane 80, the Tween 80 and the Transcutol are mixed using a Heidolph Bioblock RZR 2051 stirrer at 500 rpm for 6 minutes at room temperature.

A translucent phase is obtained into which is incorporated the progesterone until saturation under stirring at 700 rpm for 4 minutes.

Once the active principle dissolved, the hydrophile phase (purified water) is added. The mixture is homogenized with a Bioblock Heidolph RZE 2051 stirrer at 500 rpm for 5 minutes.

A solution A is thereby obtained which is saturated with clear yellowish transparent and liquid progesterone.

Progesterone Suspension Obtained with Solution A: Suspension B

| Components | % w/w |
|---|---|
| Refined sunflower oil | 20.95 |
| Montane 80 | 18.32 |
| Tween 80 | 5.24 |
| Transcutol HP | 7.85 |
| Distilled water | 2.36 |
| Progesterone | 45.28 |

Progesterone is dispersed in solution A until obtention of a suspension with 45.28% in progesterone under stirring at 700 rpm for 5 minutes with a Bioblock Heidolph RZR 2051 stirrer.

The obtained suspension is slightly viscous and white.

Suspension B Impregnation on an Inert Support

The suspension is adsorbed on an inert support such as silica (Aeroperl® 300, Degussa).

| Components | % w/w |
|---|---|
| Refined sunflower oil | 15.35 |
| Montane 80 | 13.43 |
| Tween 80 | 3.83 |
| Transcutol HP | 5.75 |
| Distilled water | 1.74 |
| Progesterone | 33.17 |
| Aeroperl 300 | 26.73 |

Adsorption is obtained with a Rotolab, Zancheta mixer-granulator.

Impregnation parameters are the following:

Paddle speed: 300 rpm

Suspension introduction time: 20 s

Homogenization time: 5 minutes.

Characterisation of the Progesterone Based Impregnated Powder

| Pharmacological Tests | Results |
|---|---|
| Flowability (Pharm. Eur. 4.2; 2.9.15) | |
| Crushability (Pharm. Eur 4.2; 2.9.15) | V10-V500 = 23 mL |
| Relative moisture (Moisture analyser MA 30 Sartorius 100° C. 15 min.) | 9.70% |
| Mean size (Laser Malvern size Mastersizer 2000 provided with a sirocco 2000 vibrator 2 bars vibrations 90%) | 30.5 µm (appendix 1) |

In Vitro Dissolution of the Progesterone Based Impregnated Powder.

The dissolution profile of the progesterone based impregnated powder improving the bioavailability and the solubilization is compared with those of Utrogestran® commercial formulation.

The dissolution test is made with an AT7 Sotax dissolutest with glass dissolution beakers.

The dissolution medium being used is a 1% Kleptose solution.

The both temperature is maintained at 37° C. and the paddle rotation speed is 150 rpm.

The dosage occurs on line through UV spectrometry.

Figure 7:
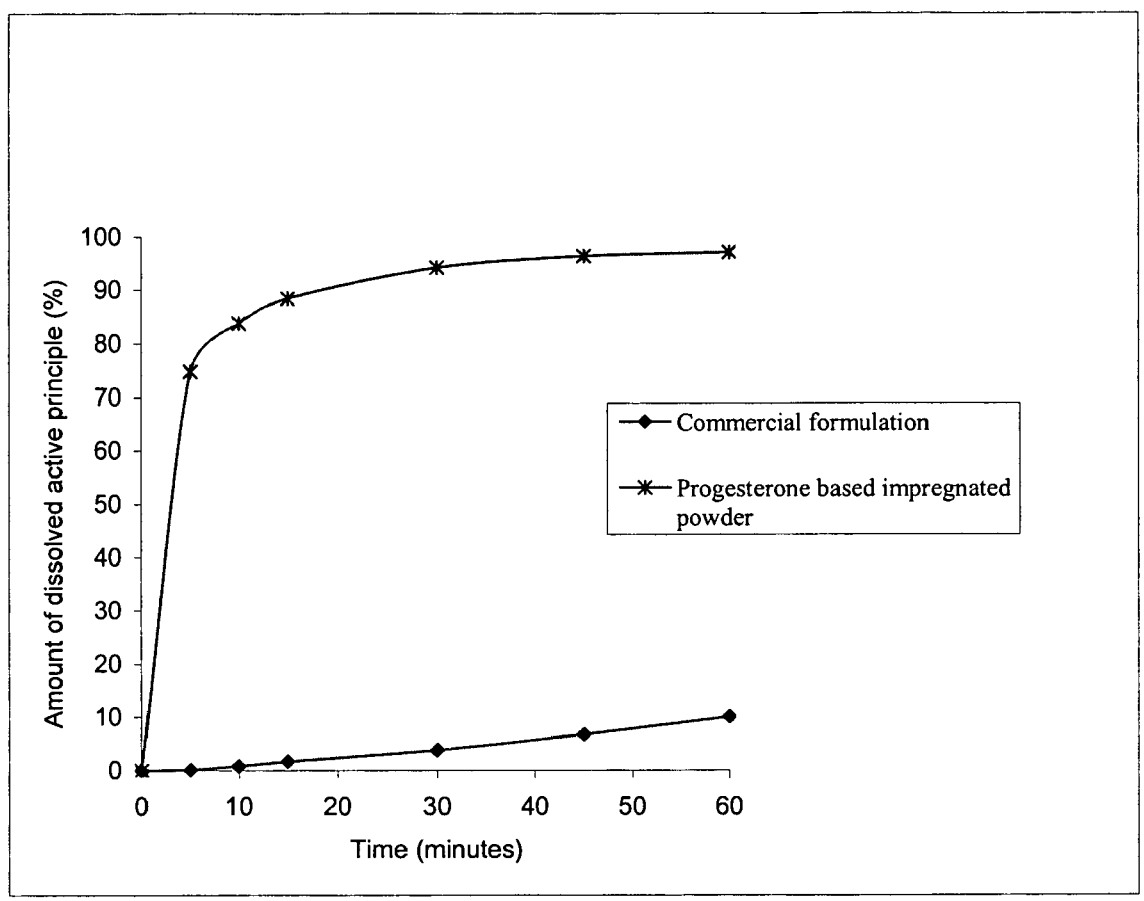

The results are represented on FIG. 7 which shows a comparison of the dissolution profile (1% Kleptose 150 rpm) of the progesterone based impregnated powder dosed at 100 mg according to the invention with a commercial formulation.

After 1 hour, the whole dose is released with the impregnated powder while only 10% of progesterone are released with the commercial formulation.

Obtention of Tablets with the Progesterone Impregnated Powder.

The impregnated powder is mixed with a diluent (Vivapur® 12 JRS Pharma) and a desintegrator (Lycatab® C, Roquette) with a Rotolab® (Zanchetta) stirrer at 150 rpm for 3 minutes.

The mixture is then tablated with an alternative Frogerais tablet making machine.

| Component | % w/w | Unitary dosage (mg) |
|---|---|---|
| Refined sunflower oil | 7.6 | 45.78 |
| Montane 80 | 6.7 | 40.36 |
| Tween 80 | 1.9 | 11.45 |
| Transcutol HP | 2.9 | 17.47 |
| Distilled water | 0.9 | 5.42 |
| Progesterone | 16.6 | 100 |
| Aeroperl 300 | 13.4 | 80.72 |
| Vivapur 12 | 45 | 271.09 |
| Lycatab C | 5 | 30.12 |
| Die shape | Elongated 14 × 8.5 R 6.5 | |
| Tablet weight | 602.41 mg | |
| Toughness | 40N | |
| Releasing time | 18 s | |
| Crumbability | 0.62% | |

In Vitro Dissolution of the Tablets;

The dissolution profile of the progesterone tablets improving the bioavailability and the solubilization is compared with those of Utrogestran® commercial formulation.

The dissolution test is made with an AT7 Sotax dissolutest with glass dissolution beackers.

The dissolution medium being used is a 1% Kleptose solution.

The bath temperature is maintained at 37° C., the paddle rotation speed is 150 rpm.

The dosage occurs on line through UV spectrometry.

Figure 8:
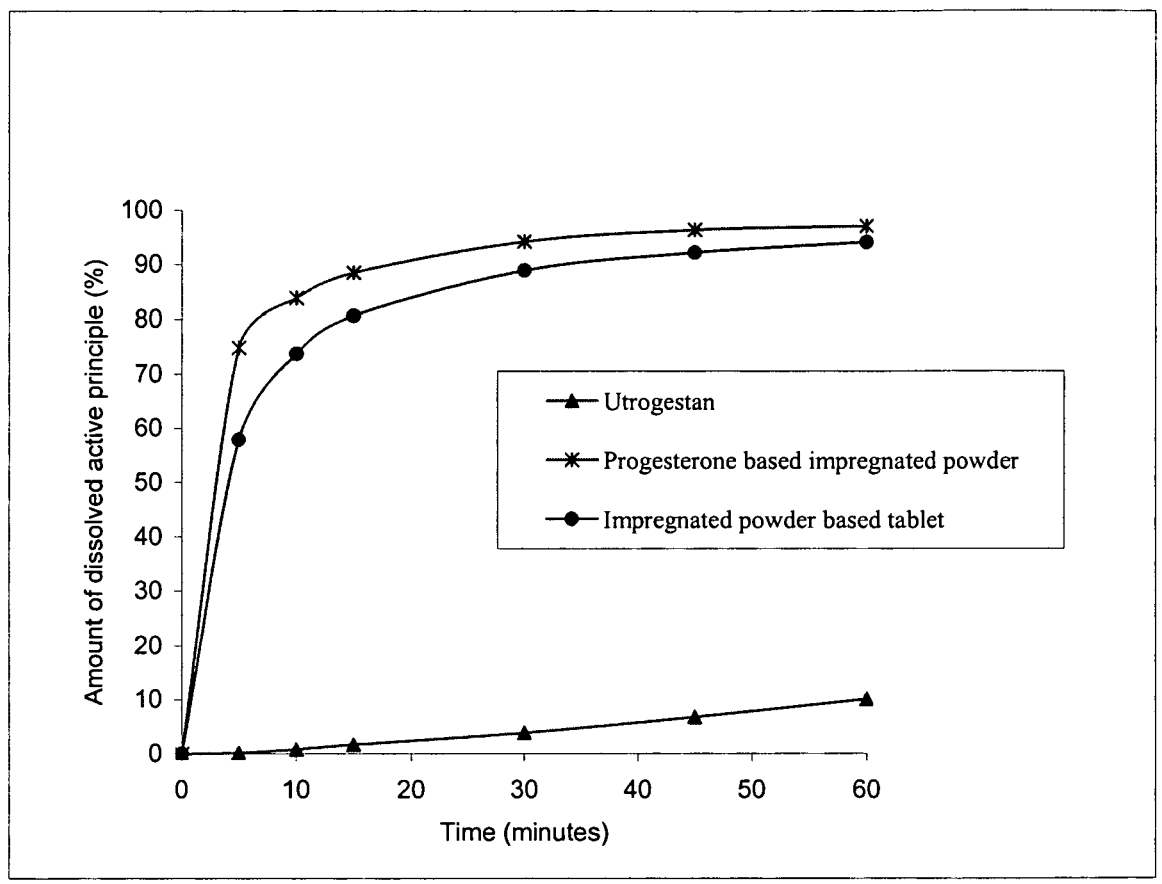

The results are represented on FIG. 8 which shows a comparison of the dissolution profile (1% Kleptose, 150 rpm, 37° C.) between respectively (i) an impregnated powder according to the invention, (ii) an impregnated powder tablet according to the invention and (iii) a commercial formulation dosed at 100 mg of progesterone.

After 60 minutes, the impregnated powder tablets release about 95% of the progesterone while only 10% of progesterone are released with the commercial formulation.

The size analysis results of the progesterone based impregnated powder are shown on FIG. 9 which indicates the size distribution of the powder particles.

EXAMPLE 5

Production of Quick Release Acyclovir Based Tablet

Acyclovir Suspension

Acyclovir is solubilized in the hydrophile phase (HCl buffer, pH 2) at 500 rpm for 10 minutes at room temperature.

The obtained A solution is clear and fluid.

The hydrophobe phase (Captex® 300, Abitec), the surfactant (Acconon® CC6, Abitec) and the co-surfactant (oleic Plurol, Gattefossé) are mixed for 5 minutes at 500 rpm at room temperature.

The obtained B solution is slightly yellowish and fluid.

The A solution saturated in Acyclovir and the B solution are mixed for 5 minutes at 500 rpm.

The obtained C mixture is fluid and slightly yellowish.

The remaining Acyclovir is put in suspension under stirring at 700 rpm during 10 minutes.

The obtained D suspension with 65% Acyclovir is white and creamy.

Said tests are made with an Heidolph Bioblock RZE 2051 stirrer.

| D Suspension Components | % w/w |
|---|---|
| Captex 300 | 11.2 |
| Acconon CC6 | 8.4 |
| Oleic Plurol | 8.4 |
| HCl buffer pH2 | 7 |
| Acyclovir | 65 |

Suspension D Impregnation on an Inert Support.

The suspension is adsorbed on an inert support such as silica (Aeroperl® 300 Degussa).

The adsorption is made with a Rotolab, Zanchetta mixer-granulator.

The impregnation parameters are the following:
Paddle speed: 250 rpm
suspension incorporating time: 20 s
homogenization time: 5 minutes

| Components | % w/w |
|---|---|
| Captex 300 | 9.21 |
| Acconon CC6 | 6.9 |
| Oleic Plurol | 6.9 |
| HCl Buffer pH 2 | 5.76 |
| Acyclovir | 53.45 |
| Aeroperl 300 | 17.78 |

Characterization of the Acyclovir Based Impregnated Powder

| Pharmacological tests | Results |
|---|---|
| Flowability (Pharm Eur 4.2; 2.9.15) | 7.02 |
| Crushability (Pharm Eur 4.2; 2.9.15) | V10-V500 = 29 mL |
| Relative moisture (moisture analyser MA 30 Sartorius, 100° C., 15 min.) | 7.44% |
| Mean size (Laser Malvern sizer Mastersizer 2000 provided With a Sirocco 2000 vibrator 2 bars, vibrations 90%) | 23.066 μm (appendix 2) |

In Vitro Dissolution of the Acyclovir Based Impregnated Powder.

The dissolution profile of the Acyclovir impregnated powder improving the bioavailability and the solubilization is compared with those of the ZOVIRAX® commercial formulation.

The dissolution test is made with an AT7 Sotax dissolutest with glass dissolution beakers.

The dissolution medium being used is a HCl solution 0.01 N.

The bath temperature is maintained at 37° C. and the paddle rotation speed is 100 rpm.

The dosage occurs on line through UV spectrophotometry.

Figure 10:
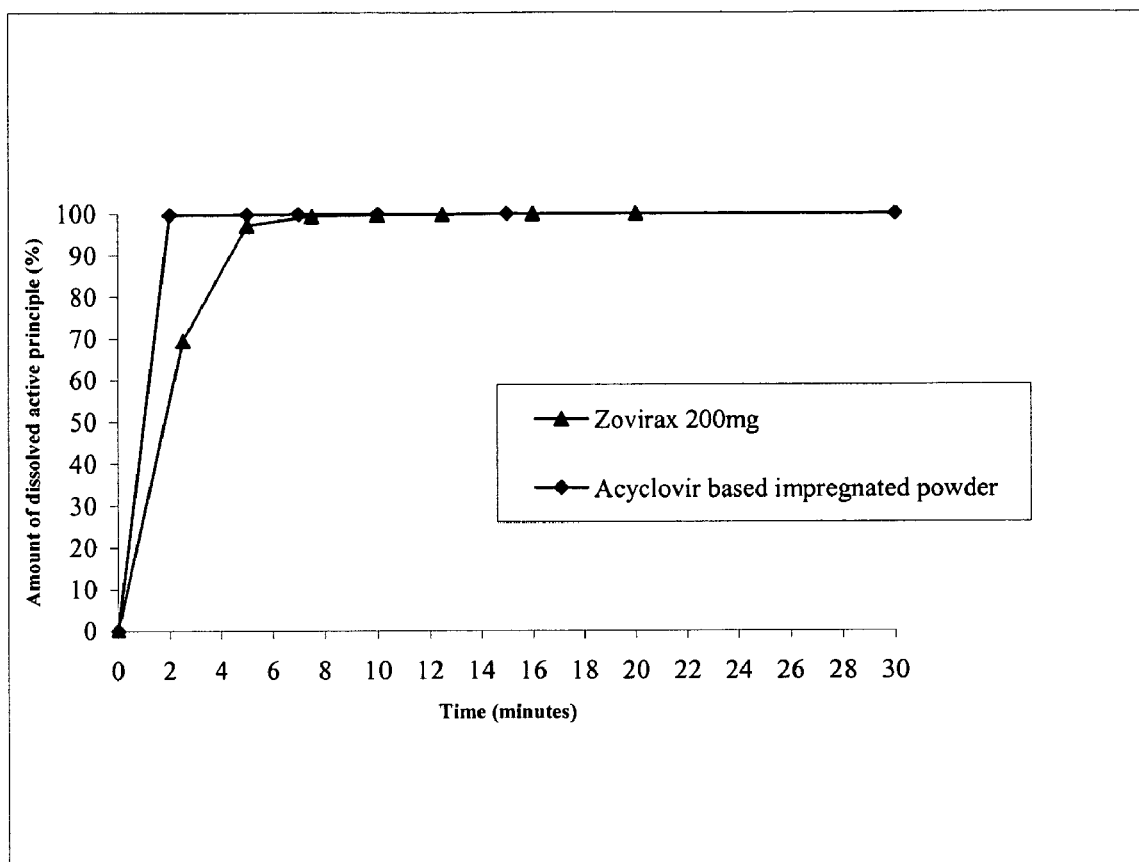

The dissolution comparative profile results are represented on FIG. 10 which shows a comparison of the dissolution profile (medium HCl 0.01 N, 100 rpm, 37° C.) of an Acyclovir based impregnated powder according to the invention with a commercial Acyclovir formulation dosed at 200 mg.

100% of the dose is released in less than 2 minutes with the impregnated powder.

After 2 minutes the commercial formulation releases only 55% of Acyclovir.

Obtention of Tablets with the Acyclovir Impregnated Power

The impregnated powder is mixed with a diluent (Vivapur® 12, JRS Pharma) and a desintegrator (Lycatab® C, Roquette) with a Rotolab® (Zanchetta) stirrer at 150 rpm for 3 minutes.

The mixture is then tableted with an alternative Frogerais tablet making machine.

| Components | % w/w | Unitary dosage (mg) |
|---|---|---|
| Captex 300 | 4.6 | 34.42 |
| Acconon CC6 | 3.45 | 25.81 |
| Oleic Plurol | 3.45 | 25.81 |
| HCl buffer pH2 | 2.88 | 21.55 |
| Acyclovir | 26.73 | 200 |
| Aeroperl 300 | 8.89 | 66.52 |
| Vivapur 12 | 45 | 336.70 |
| Lycatab C | 5 | 37.41 |
| Die shape | 19 × 8R8, elongated form | |
| Tablet weight | 748.22 mg | |
| Toughness | 48 N | |
| Releasing time | 13 s | |
| Crumbability | 0.9% | |

In Vitro Dissolution of the Impregnated Powder Based Tablets.

The dissolution profile of the impregnated powder based tablets improving the bioavailability and the solubilization is compared with those of Zovirax® commercial formulation.

The dissolution test is made with an AT7 Sotax dissolutest with glass dissolution beakers.

The dissolution medium being used is a HCl 0.01 N solution.

The both temperature is maintained at 37° C., the paddle rotation speed is 100 rpm.

The dosage occurs on line through UV spectrophotometry.

Figure 11:
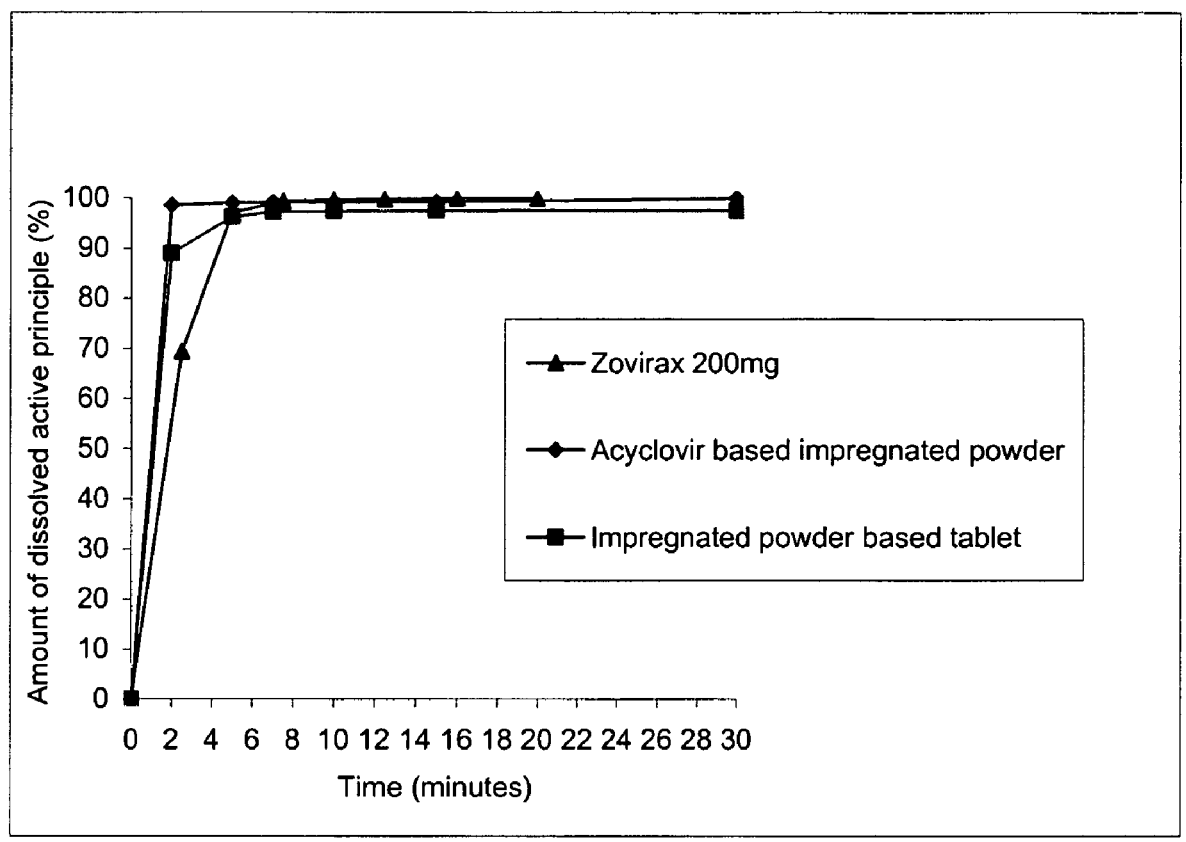

The results of the dissolution profile are represented on FIG. 11 which shows a comparison of the dissolution profile (HCl 0.01 N, 100 rpm) between (i) an acyclovir based impregnated powder according to the invention, (ii) a tablet made from such impregnated powder and (iii) a ZOVIRAX® commercial formulation dosed at 200 mg.

The size analysis results of said Acyclovir based impregnated film powder are represented on FIG. 12 which shows the size distribution of the said powder particules.

EXAMPLE 6

Production of a Quick Release Co-micronized Fenofibrate Based Tablet with Sodium Lauryl Sulfate.

Capryol® 90 (Gattefossé) Acconon® CC6 (Abitec), Transcutol® (Gattefossé) are mixed with a Bioblock Heidolph RZE 2051 stirrer at 500 rpm for 5 minutes at room temperature.

A translucent phase is obtained into which is incorporated co-micronized Fenofibrate until saturation with stirring at 700 rpm for 10 minutes.

Once the active principle dissolved, the hydrophile phase (purified water) is added. The mixture is homogeneized with a Bioblock Heidolph RZE 2051 stirrer at 500 rpm for 5 minutes.

A solution A is thereby obtained which is saturated with clear yellowish transparent and liquid co-micronized Fenofibrate.

The remaining co-micronized Fenofibrate is dispersed in solution A until obtention of a suspension dosed at 41.52% in co-micronized Fenofibrate with stirring at 700 rpm for 10 minutes with a bioblock Heidolph R2R 2051 stirrer.

The obtained B suspension is viscous and white.

| Suspension B components | % /w |
|---|---|
| Capryol 90 | 33.32 |
| Acconon CC6 | 6.67 |
| Transcutol | 15.55 |
| Distilled water | 2.94 |
| Co-micronized Fenofibrate with SLS (Fenofibrate content: 96.56% | 41.52 |

The suspension is adsorbed on an inert support such as silica (Aeroperl® 300 Degussa).

Adsorption is obtained with a Rotolab, Zanchetta mixer-granulator.

Impregnation parameters are the following:
Paddle speed: 300 rpm
Suspension introduction time: 20 seconds
Homogenization time: 5 minutes.

| Components | % w/w |
|---|---|
| Capryol 90 | 23.65 |
| Acconon CC6 | 4.73 |
| Transcutol | 11.03 |
| Distilled water | 2.09 |
| Co-micronized Fenofibrate | 29.47 |
| Aeroperl 300 | 29.0 |
| Remark | White powder with a good flow |

In Vitro Dissolution of the Co-micronized Fenofibrate Based Impregnated Powder.

The dissolution profile of the co-micronized Fenofibrate based impregnated powder improving the bioavailability and the solubilization is compared with those of the Lipanthyl commercial formulation.

The dissolution test is made with an AT7 Sotax dissolutest with glass dissolution beakers.

The dissolution medium being used is a sodium lauryl sulfate 0.1M solution.

The both temperature is maintained at 37° C. and the paddle rotation speed is 100 rpm.

The dosage occurs on line through UV spectrophotometry.

Figure 13:
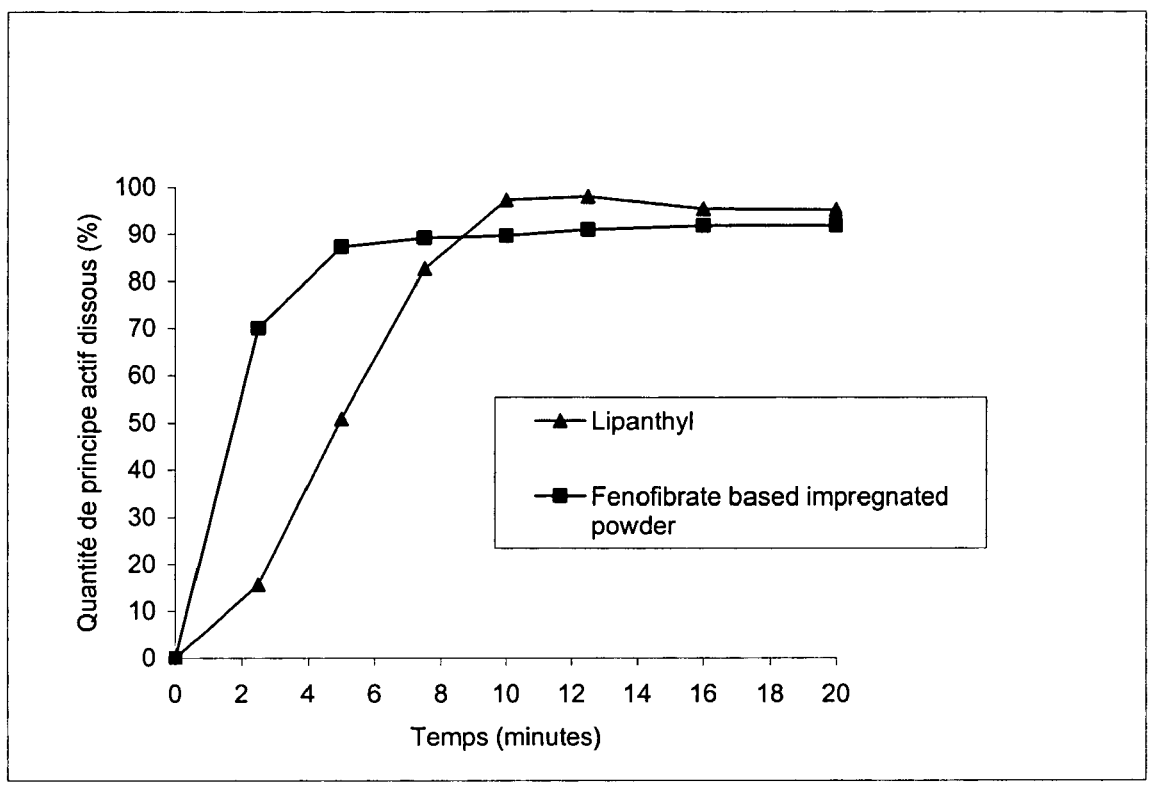

The in vitro dissolution profile results are represented on FIG. 13 which shows a comparison of the dissolution profiles (SLS 0.1M, 100 rpm) between a Fenofibrate based impregnated powder according to the invention and a LIPANTHYL® commercial formulation dosed at 160 mg.

The Fenofibrate releasing is quicker during the six first minutes with the impregnated powder than with the commercial formulation.

The invention claimed is:

1. An impregnated powder for increasing the bioavailability and/or the solubility of at least one active principle comprising a solid inert support, in a particle form impregnated by a liquid medium comprising a hydrophobic phase and a hydrophilic phase, at least one surfactant and at least one active principle wherein said active principle(s) is (are) dissolved in one of said hydrophilic or hydrophobic phases, and in the form of a suspension in the other one of said phases, wherein the phase in which the active principle(s) is (are) dissolved is an active principle saturated solution.

2. An impregnated powder according to claim 1, wherein the liquid medium moreover comprises at least one co-surfactant.

3. An impregnated powder according to claim 1, wherein the co-surfactant(s) is (are) selected from the group consisting of alcohols, glycol ethers, glycol and the derivatives thereof, propylene glycol and the derivatiyes thereof, lauryl esters of propylene glycol, polyglycerol and the derivatives thereof, oleyl esters of polyglycerol and ethyldiglycol.

4. An impregnated powder according to claim 1, wherein the surfactant(s) is (are) selected from the group consisting of non ionic, anionic, cationic and amphiphilic surfactants.

5. An impregnated powder according to claim 1, wherein the surfactant(s) is (are) at least 1%, based on the weight of the liquid medium.

6. An impregnated powder according to claim 1, wherein the hydrophobic phase of the liquid medium is selected from the group consisting of vegetable oils mineral oils, animal oils, synthetic oils, monoglycerides, diglycerides, triglycerides, fatty alcohols and derivatives thereof, polyol esters, liquid paraffin, long chain hydrocarbons, tocopherol and derivatives thereof, aliphatic fatty acids, fatty acid esters, silicone oils, phospholipid compounds and derivatives thereof, and mixtures thereof.

7. An impregnated powder according to claim 1, wherein the hydrophilic phase of the liquid medium is selected from the group consisting of water, hydroalcoholic mixtures, saline aqueous solutions, buffered aqueous solutions, water-polyethylene glycol mixtures, water-glycerol mixtures, glucose aqueous solutions and water-propylene glycol mixtures.

8. An impregnated powder according to claim 1, wherein the active material(s) is (are) selected from the group consisting of hydrosoluble, liposoluble and amphiphilic active materials.

9. A dry impregnated powder according to claim 1, wherein the active material(s) is (are) selected from the group consisting of pharmaceutical agents, parapharmaceutical agents, cosmetic agents, and food ingredients.

10. An impregnated powder according to claim 9, wherein the active material(s) is (are) selected from the group consisting of active materials used in the following pharmacotherapeutic families: allergology, anesthesia/resuscitation, cancerology and hematology, cardiology and angiology, contraception and pregnancy interruption, dermatology, endocrinology, gastroentero-pathology, gynecology, immunology, infectiology, metabolism and nutrition, neurology/psychiatry, ophthalmology, otorhinolaryngology, pneumology, rhumatology, stomatology, toxicology, urology/ nephrology, as well as analgesic and antispasmodic drugs, anti-inflammatory drugs, the contrast products used in radiology, hemostatics and blood treatment products and derivatives thereof.

11. An impregnated powder according to claim 1, wherein the liquid medium contains from 0.001% to 70% by weight of active material based on the total weight of the liquid system.

12. An impregnated powder according to claim 1, wherein the liquid medium moreover comprises at least one adhesive agent.

13. An impregnated powder according to claim 1, wherein the liquid medium moreover comprises at least one penetration builder.

14. An impregnated powder according to claim 1, wherein the liquid medium moreover comprises at least one thermoreversible polymer.

15. An impregnated powder according to claim 1, wherein the liquid medium is 1% to 99% based on the total weight of the impregnated powder.

16. An impregnated powder according to claim 1, wherein the inert solid support is selected from the group consisting of natural silicas, silica gels, fumed silicas, precipitated silicas, clays, talc, magnesium hydroxide, aluminum hydroxide, magnesium oxide, maltodextrins, cyclodextrins, cellulose derivatives and mixtures thereof.

17. An impregnated powder according to claim 1, wherein it comprises one or more builders selected from the group consisting of flavoring agents, perfumes, essential oils, dyes, antioxidants, preservatives, sweeteners and fillers.

18. A method for producing an impregnated powder comprising the steps of:
   obtaining a liquid medium comprising an hydrophilic phase and a hydrophobic phase, at least one surfactant and at least one dissolved active principle in at least one of said phases and present in at least one of said phases in the form of a suspension, wherein the phase in which the active principle(s) is (are) dissolved is an active principle saturated solution;
   mixing a suitable amount of the liquid medium and a suitable amount of an inert solid support in a particle form liable to adsorb the liquid medium; and
   recovering an impregnated powder.

19. A method according to claim 18, wherein the liquid medium is obtained by solubilizing an amount of active principle(s) in one of said phases, mixing to the phase containing the dissolved active principle(s) in the other of said phases, and adding an additional amount of active principle(s) to the mixture of two phases in order to obtain a suspension.

20. A method according to claim 18, wherein the liquid medium is obtained by mixing the two phases and adding an amount of active principle(s) sufficient to obtain a dissolution of the active principle(s) in at least one of the phases and a suspension of the active principle(s) in at least one of the other phases.

21. An impregnated powder according to claim 1, wherein the impregnated powder is supplied in a packaging adapted to the administration of all or part of such an impregnated powder.

22. An impregnated powder according to claim 1, wherein all or part of such an impregnated powder is provided in a form selected from the group consisting of bags, stick-packs, wipes, capsules, pressurized flasks, non pressurized flasks, and powder sprays provided through a nasal, oral or vaginal route.

23. An impregnated powder according to claim 1, wherein all or part of such an impregnated powder is provided in a form selected from the group consisting of bare or blistered tablets, sugar-coated tablets, coated tablets (soluble coating, pH-dependent or independent coating, with a gastric, intestinal or other release), matricial tablets, osmotic tablets, multilayered tablets, effervescent tablets, dual core tablets, floating tablets, forms with gastric residence and/or floating forms, mucoadhesive forms, capsules, powders, multiparticle forms such as granules, coated microgranules (sugar-coated, with a soluble, pH-dependent coating) or not coated microgranules, mucoadhesive forms, and atomized solids.

24. An impregnated powder according to claim 1, wherein it is as a galenic form with a release profile selected from the group consisting of immediate, modified, delayed, bimodal and pulsed release.

25. A method of preparing a pharmaceutical dosage form comprising the impregnated powder according to claim 1, comprising:
   providing said impregnated powder;
   providing one or more pharmaceutically-acceptable excipients; and
   forming a pharmaceutical dosage form selected from the group consisting of bare or blistered tablets, sugar-coated tablets, coated tablets (soluble coating, pH-dependent or independent coating, with a gastric, intestinal or other release), matricial tablets, osmotic tablets, multilayered tablets, effervescent tablets, dual core tablets, floating tablets, forms with gastric residence and/or floating forms, mucoadhesive forms, capsules, powders, multiparticle forms such as granules, coated microgranules (sugar-coated, with a soluble, pH-dependent coating) or not coated microgranules, mucoadhesive forms and atomized solids by combining said one or more pharmaceutically-acceptable excipients with the impregnated powder of claim 1.

26. An impregnated powder according to claim 5, wherein the surfactant(s) is (are) 2% to 70%, based on the weight of the liquid microemulsion.

27. An impregnated powder according to claim 26, wherein the surfactant(s) is (are) 10% to 60%, based on the weight of the liquid microemulsion.

28. An impregnated powder according to claim 11, wherein the liquid medium contains from 0.5% to 60% by weight of active material based on the total weight of the liquid system.

29. An impregnated powder according to claim 28, wherein the liquid medium is 20% to 90%, based on the total weight of the impregnated powder.

30. An impregnated powder according to claim 29, wherein the liquid medium is 40% to 90% based on the total weight of the impregnated powder.

31. An impregnated powder according to claim 30, wherein the liquid medium is 50% to 80% based on the total weight of the impregnated powder.

* * * * *